US009527876B2

United States Patent
Shu et al.

(10) Patent No.: US 9,527,876 B2
(45) Date of Patent: Dec. 27, 2016

(54) PRODRUGS OF BICYCLIC SUBSTITUTED PYRIMIDINE TYPE PDE-5 INHIBITORS

(71) Applicant: Xuanzhu Pharma Co., Ltd., Shandong (CN)

(72) Inventors: Chutian Shu, Shandong (CN); Yongqian Wu, Shandong (CN)

(73) Assignee: Xuanzhu Pharma Co., Ltd., Shandong (CN)

( * ) Notice: Subject to any disclaimer, the term of this patent is extended or adjusted under 35 U.S.C. 154(b) by 0 days.

(21) Appl. No.: 14/780,718

(22) PCT Filed: Mar. 28, 2014

(86) PCT No.: PCT/CN2014/074268
§ 371 (c)(1),
(2) Date: Sep. 28, 2015

(87) PCT Pub. No.: WO2014/154168
PCT Pub. Date: Oct. 2, 2014

(65) Prior Publication Data
US 2016/0046654 A1 Feb. 18, 2016

(30) Foreign Application Priority Data
Mar. 29, 2013 (CN) .......................... 2013 1 0105971

(51) Int. Cl.
*A61K 31/675* (2006.01)
*C07F 9/6558* (2006.01)
*A61K 45/06* (2006.01)

(52) U.S. Cl.
CPC ......... *C07F 9/65583* (2013.01); *A61K 31/675* (2013.01); *A61K 45/06* (2013.01)

(58) Field of Classification Search
CPC .................. C07F 9/65583; A61K 31/675
See application file for complete search history.

(56) References Cited

U.S. PATENT DOCUMENTS

| 6,797,709 | B2 * | 9/2004 | Yamada | C07D 239/48 514/231.5 |
| 7,087,597 | B1 * | 8/2006 | Miwa | C07D 401/14 514/212.08 |
| 7,220,736 | B2 * | 5/2007 | Yamada | C07D 239/48 514/211.1 |
| 7,273,868 | B2 * | 9/2007 | Yamada | C07D 239/48 514/249 |
| 8,716,298 | B2 * | 5/2014 | Lee | A61Q 19/08 514/262.1 |
| 8,980,904 | B2 * | 3/2015 | Wu | 514/273 |
| 9,155,691 | B2 * | 10/2015 | Lee | A61Q 19/08 |
| 9,359,371 | B2 * | 6/2016 | Wu | C07D 401/14 |
| 2003/0229089 | A1 * | 12/2003 | Yamada | C07D 239/48 514/230.5 |
| 2003/0229095 | A1 * | 12/2003 | Yamada | C07D 239/48 514/252.03 |
| 2008/0027037 | A1 * | 1/2008 | Yamada | C07D 239/42 514/211.1 |
| 2015/0232474 | A1 | 8/2015 | Wu et al. | |

FOREIGN PATENT DOCUMENTS

| CN | 102372697 A | 3/2012 |
| CN | 102887889 A | 1/2013 |
| EP | 1 223 170 A1 | 7/2002 |
| WO | WO 01/19802 A1 | 3/2001 |
| WO | WO 2014/026467 A1 | 2/2014 |

OTHER PUBLICATIONS

International Search Report for Application No. PCT/CN2014/074268 dated Jun. 25, 2014, 6 pages.
English language abstract and machine-assisted English translation for CN 102372697 extracted from espacenet.com database on Oct. 29, 2015, 58 pages.
English language abstract for CN 102887889 extracted from espacenet.com database on Oct. 29, 2015, 1 page.
English language abstract for WO 01/19802 extracted from espacenet.com database on Oct. 29, 2015, 2 pages.
English language abstract for WO 2014/026467 extracted from espacenet.com database on Oct. 29, 2015, 2 pages.
Jarkko, Rautio et al., "Prodrugs: Design and Clinical Applications", Nature Reviews, Drug Discovery, vol. 7, No. 3, Feb. 1, 2008, pp. 255-270, XP055227338, ISSN: 1474-1776, DOI 10.1038/nrd2468.
Huttunen, K.M. et al., "Prodrugs—From Serendipity to Rational Design", Pharmacological Reviews, vol. 63, No. 3, Sep. 1, 2011, pp. 750-771, XP055073805, ISSN: 0031-6997, DOI: 10.1124/pr.110.003459.

\* cited by examiner

*Primary Examiner* — Alexander R Pagano
(74) *Attorney, Agent, or Firm* — Howard & Howard Attorneys PLLC

(57) ABSTRACT

Provided are prodrugs of a bicyclic substituted pyrimidine type PDE-5 inhibitors, pharmaceutically acceptable salts or stereoisomers thereof. Also provided are methods for preparing these prodrug compounds, pharmaceutical preparations, and pharmaceutical compositions, as well as a use of these compounds, pharmaceutical preparations and pharmaceutical compositions in the manufacture of medicaments for treatment and/or prophylaxis of sexual dysfunction and lower urinary tract symptoms.

17 Claims, No Drawings

PRODRUGS OF BICYCLIC SUBSTITUTED PYRIMIDINE TYPE PDE-5 INHIBITORS

RELATED APPLICATIONS

This application is the National Stage of International Patent Application No. PCT/CN2014/074268, filed on Mar. 28, 2014, which claims priority to and all the advantages of Chinese Patent Application No. 201310105971.8, filed on Mar. 29, 2013, the content of which is incorporated herein by reference.

1. TECHNICAL FIELD

The present invention relates to technology field of medicine and pharmacy, specifically relates to prodrugs of bicyclic substituted pyrimidine type PDE-5 inhibitors, pharmaceutically acceptable salts or stereoisomers thereof, methods for preparing these prodrug compounds, pharmaceutical preparations thereof, pharmaceutical compositions thereof, and a use of these compounds in the manufacture of medicaments for enhancing cGMP signal transduction. In particular, the present invention relates to the use of these compounds in the manufacture of medicaments for treatment and/or prophylaxis of sexual dysfunction and lower urinary tract symptoms.

2. BACKGROUND ART cGMP (guanosine-3',5'-cyclic monophosphate, cyclic GMP) is a cyclic nucleotide, exists in cells of animals and plants, is an intracellular second messenger involved in various cell reactions, and it can be hydrolyzed by PDE-5 (phosphodiesterase-5). When PDE-5 is inhibited, the level of cGMP would increase and result in many physiological effects such as vascular smooth muscle diastole. Hence, PDE-5 inhibitors can be used for treatment of diseases caused by cGMP signal transduction disorder, including hypertension, heart failure, pulmonary arterial hypertension, erectile dysfunction, prostatic hyperplasia and female sexual dysfunction, etc.

Erectile dysfunction (ED) is the most common sexual dysfunction in adult males, referring to a disease that penis is continuously unable to achieve or maintain an erection so as to enjoy sexual life. ED includes organic ED, psychological ED and mixed ED. Although ED is not lethal disease, it has a strong impact on life quality and goodwill between spouses.

There are many therapies for treatment of ED, mainly comprising three aspects: peripheral drug therapies, central drug therapies and genetic therapies. Peripheral drug therapies principally refer to applications of phosphodiesterase-5 inhibitors (e.g., sildenafil), as well as applications of papaverine, soluble guanylate cyclase activators, Rho kinase agonists and topical alprostadil. Central drug therapies refer to therapies using drugs such as dopamine receptor agonists, a adrenergic receptor antagonists, 5-hydroxytryptamine (5-HT) receptor agonists, oxytocin and oxytocin receptor agonists. In genetic therapies, on the basis that ion channel is an important material basis for regulating the tension of corpus cavernosum smooth muscle, plasmid vector hMaxi-K (pVAX-hSLO) expressing hSlo gene is injected into corpus cavernosum, which expresses in corpus cavernosum smooth muscle, generates more potassium channels so as to render corpus cavernosum relaxation.

Currently, there are many therapies for treatment of ED, among which phosphodiesterase-5 (PDE-5) inhibitors with sildenafil (Vigra) as representative are first-line drugs for treatment of ED, and are the most popular therapy in patients. At present, PED-5 inhibitors in market include Sildenafil, Vardenafil, Tadalafil, Udenafil and Avanafil, etc. These drugs are taken orally and conveniently, act quickly and have good efficiency. Among them, Sildenafil and Tadalafil are most important profitable products of Pfizer and Eli Lilly Company, respectively. Hence, these drugs have huge market volume.

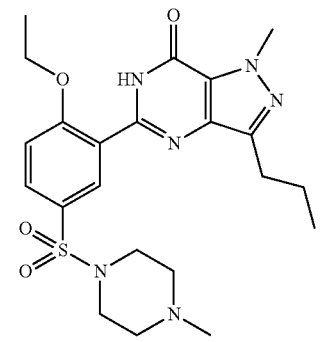
Sildenafil

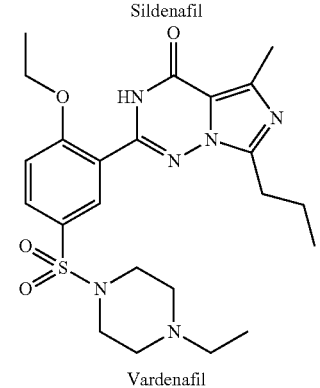
Vardenafil

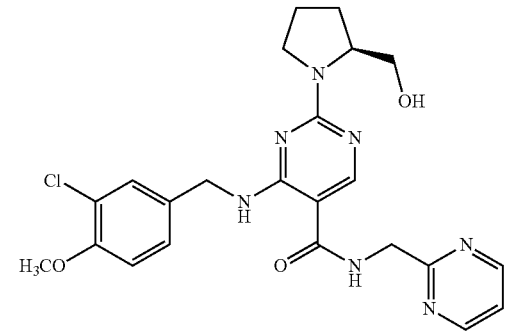
Avanafil

In patent application WO200119802 (published on 2001 Mar. 22) of Tanabe Seiyaku CO., LTD, the following compounds are disclosed:

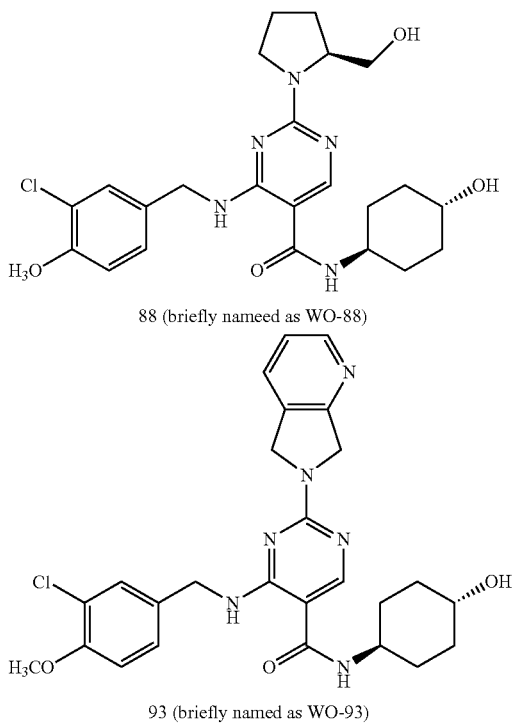

88 (briefly nameed as WO-88)

93 (briefly named as WO-93)

In view of epidemiology, many elderly male patients have ED accompanied with other diseases of genitourinary system, such as lower urinary tract symptoms (LUTS) including benign prostatic hyperplasia (BPH), overactive bladder syndrome (OAB), etc. These diseases bring about tremendous distress to the elderly patients and seriously affect their life. The pathological analysis shows ED and LUTS have same pathogenesis, and both of them associate with smooth muscle contraction or smooth muscle cell proliferation. Thus, it is possible to use PDE-5 inhibitor to treat LUTS with same pathogenesis. Tadalafil has been approved by FDA for use in the treatment of benign prostatic hyperplasia.

With the clinical application of PDE-5 inhibitors, some latent safety problems gradually appear. Among the drugs, Sildenafil and Vardenafil not only have inhibition on PDE-5 but also have a certain inhibitory effect on PDE-6, which affects retinal function, so these two drugs may influence human vision, and especially more reports relate to Sildenafil in this aspect. Therefore, these two drugs have poor selectivity on PDE-5. Tadalafil has better selectivity on PDE-6, but still has inhibition effects on PDE-11 in some extent. Although the clinical pharmacological effects of PDE-11 are unknown, there is still latent risk. Some documents report Tadalafil may cause osphyalgia, while more researches are still in need to determine its relevance to PDE-11. In addition, Vardenafil has a low bioavailability and requires an increased dosage of administration, which is disadvantage for long-term medication. The half-life of Tadalafil, as long as about 16 h in human, may readily result in drug interaction if a patient takes other drugs simultaneously, for example, when nitrate drugs and Tadalafil are used together, blood pressure may drop too much in patients, thereby causing life risk.

Avanafil belongs to the second generation of PDE-5 inhibitors, which has good selectivity to PDE-6, with the ration PDE-6/5 of 120. Moreover, it does not inhibit PDE-11, which ensures the safety for clinical treatment. However, this drug has poor enzymatic activity in vitro, its clinical dosage is very high (50 mg, 100 mg and 200 mg), higher than that of Sildenafil, Vardenafil and Tadalafil, which constitutes a safety hazard for clinical treatment in patients. In addition, with the increase of dosage, therapeutic cost increases as well. So Avanafil should be further improved at least in view of pharmacoeconomics. The most common adverse reactions in clinical research reports include headache, flush, nasal congestion, nasopharyngitis or backache. A rare side effect of Avanafil is sudden decrease or loss of eyesight of the men taking this drug. Avanafil has relatively low bioavailability, high clinical dosage, short half-life (as short as about 1.2 h in vivo), so it can only be used for single treatment of erectile dysfunction, and is not suitable for treatment of BPH, OAB and so on. Hence, it is significant to develop PDE-5 inhibitors with high selectivity, more potent pharmacological activity, high bioavailability, higher safety and appropriate (longer but not too much longer) half-life so as to improve life quality (treatment of ED, BPH and LUTS) of elderly patients.

However, most of these compounds have disadvantage of poor water solubility, which brings about difficulty in delivering drug to patients, such as high pill burden. The low water solubility of compounds is disadvantageous to the formation of preparations, cosolvents such as surfactants may have to be used. It results in that the doses of these compounds are strictly restricted in some specific liquid dosage forms, such as the dose of liquid encapsulated in soft gelatin capsules. In order to improve water solubility of these compounds, the drug load per unit dose for the compounds may have to be increased, which brings about serious side-effects on human body. In addition, high pill burden would further increase the daily dosage of patients, which may impair compliance of patients, and thus the optimal therapeutic effects of medication may not be achieved. Moreover, the poor solubility of these compounds means potential possibility of crystallization and precipitation from solution under storage and/or transportation conditions, which may cause safety problems of drugs in clinical implications.

In summary, it is now a hotspot of research to find compounds inhibiting PDE-5, especially with good activity, high selectivity and capable of solving poor solubility of these compounds, to effectively overcome difficulties of preparing various preparations such as oral, intravenous injection and intramuscular injection preparations, and to broaden clinical application.

3. CONTENTS OF THE INVENTION

In the Patent Application PCT/CN2013/0009533, the inventors provide a group of PDE-5 inhibitors with good activity and high selectivity. In the present invention, the compounds of Formula (I) as disclosed in PCT/CN2013/000953 are prepared into prodrugs. These prodrugs improved physical and chemical properties of original compounds, selectivity to target site, and pharmacokinetics such as absorption, distribution, transportation and metabolism in vivo. It is very important for the development of preparations and crystal forms. Thus, the objective of the present invention is to provide prodrugs of bicyclic substituted pyrimidine type PDE-5 inhibitors. Specifically, the present invention relates to:

(1) A compound of Formula (I), pharmaceutically acceptable salts or stereoisomers thereof:

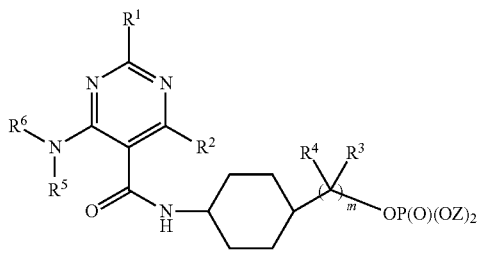

wherein $R^1$ represents 6- or 7-membered nitrogen-containing fused heterocyclyl, 7- to 12-membered nitrogen-containing spiral heterocyclyl, or 7- to 12-membered nitrogen-containing bridged heterocyclyl, any of which is optionally substituted with 1-4 substituent groups, and $R^1$ links to pyrimidine ring via N atom, the substituent groups are selected from halogen atoms, cyano, amino, hydroxyl, $C_{1-6}$ alkyl, halo $C_{1-6}$ alkyl, hydroxyl $C_{1-6}$ alkyl, $C_{1-6}$ alkoxy, $C_{1-6}$ alkylcarbonyl or $C_{1-6}$ alkoxycarbonyl;

$R^2$ represents hydrogen atom, hydroxyl, amino, cyano, $C_{1-6}$ alkylamino, di($C_{1-6}$ alkyl)amino, $C_{1-6}$ alkyl, halo $C_{1-6}$ alkyl, hydroxyl $C_{1-6}$ alkyl or $C_{1-6}$ alkoxy;

$R^3$ and $R^4$ each independently represent hydrogen, or $C_{1-6}$ alkyl optionally substituted with 1-3 halogen atoms, hydroxyl or carboxyl;

m is 0 to 3;

Z is hydrogen, or a cation of inorganic base or organic base capable of forming a salt with phosphoric acid;

$R^5$ and $R^6$ each independently represent hydrogen atom or

Q represents a bond, or optionally substituted $C_{1-6}$ alkylidene, the substituent groups are selected from halogen atoms, hydroxyl, $C_{1-6}$ alkyl, amino, cyano, nitro or $C_{1-6}$ alkoxy;

$R^7$ is selected from 6- to 14-membered aryl, 5- to 7-membered heterocyclyl or 8- to 10-membered fused cyclyl, any of which is optionally substituted with 1-4 substituent groups, the substituent groups are selected from halogen atoms, hydroxyl, $C_{1-6}$ alkyl, halo $C_{1-6}$ alkyl, carboxyl $C_{1-6}$ alkyl, $C_{2-6}$ alkenyl, $C_{2-6}$ alkynyl, $C_{1-6}$ alkoxy, halo $C_{1-6}$ alkoxy, amino, $C_{1-6}$ alkylamino, di($C_{1-6}$ alkyl)amino, cyano, nitro, $C_{1-6}$ alkylcarbonyl, sulfonylamino or $C_{1-6}$ alkylsulfonylamino.

(2) A compound of Formula (I) of (1), pharmaceutically acceptable salts or stereoisomers thereof:

$R^2$ is preferably hydrogen atom, hydroxyl or methyl; and $R^6$ is preferably hydrogen atom.

(3) A compound of Formula (I) of (1) to (2), pharmaceutically acceptable salts or stereoisomers thereof:

$R_3$ is preferably hydrogen; $R^4$ is preferably hydrogen;

m is preferably 0, 1 or 2; and

Z is preferably hydrogen, or sodium ion.

(4) A compound of Formula (I) of (1) to (3), pharmaceutically acceptable salts or stereoisomers thereof:

wherein $R^5$ represents

Q is selected from $C_{1-6}$ alkylidene, $R^7$ is selected from 6- to 10-membered aryl, 5- to 7-membered heterocyclyl or 8- to 10-membered fused cyclyl, any of which is optionally substituted with 1-4 substituent groups, the substituent groups are selected from halogen atoms, hydroxyl, $C_{1-6}$ alkyl, halo$C_{1-6}$ alkyl, carboxyl $C_{1-6}$ alkyl, $C_{1-6}$ alkoxy, halo $C_{1-6}$ alkoxy, amino, $C_{1-6}$ alkylamino, di($C_{1-6}$ alkyl)amino, cyano, nitro, $C_{1-6}$ alkylcarbonyl, sulfonylamino or $C_{1-6}$ alkylsulfonylamino.

(5) A compound of Formula (I) of (1) to (4), pharmaceutically acceptable salts or stereoisomers thereof:

wherein $R^1$ represents 6- or 7-membered nitrogen-containing fused heterocyclyl, 7- to 12-membered nitrogen-containing spiral heterocyclyl, or 7- to 12-membered nitrogen-containing bridged heterocyclyl, any of which is optionally substituted with 1-4 substituent groups, and $R^1$ links to pyrimidine ring via N atom, the substituent groups are selected from halogen atoms, cyano, amino, hydroxyl, $C_{1-6}$ alkyl, halo $C_{1-6}$ alkyl, hydroxyl $C_{1-6}$ alkyl, $C_{1-6}$ alkoxy, $C_{1-6}$ alkylcarbonyl or $C_{1-6}$ alkoxycarbonyl.

(6) A compound of Formula (I) of (1) to (5), pharmaceutically acceptable salts or stereoisomers thereof:

wherein $R^1$ is selected from 6- or 7-membered nitrogen-containing fused heterocyclyl, 7- to 10-membered nitrogen-containing spiral heterocyclyl, or 7- to 8-membered nitrogen-containing bridged heterocyclyl, any of which is optionally substituted with 1-3 substituent groups, and $R^1$ links to pyrimidine ring of Formula (I) via N atom, the substituent groups are selected from halogen atoms, cyano, amino, hydroxyl, $C_{1-4}$ alkyl, halo$C_{1-4}$ alkyl, hydroxyl $C_{1-4}$ alkyl, or $C_{1-4}$ alkoxy;

$R^3$ and $R^4$ each independently are hydrogen;

m is 0, 1 or 2;

Z is hydrogen, or sodium ion;

$R^5$ represents -Q-$R^7$,

Q is selected from $C_{1-4}$ alkylidene, $R^7$ is selected from phenyl, 5- to 7-membered heterocyclyl or 8- to 10-membered fused cyclyl, any of which is optionally substituted with 1-3 substituent groups, the substituent groups are selected from fluorine atom, chlorine atom, methyl, trifluoromethyl, methoxy, ethoxy, trifluoromethoxy, dimethylamino or carboxymethyl;

$R^2$ is selected from hydrogen atom;

$R^6$ is selected from hydrogen atom.

(7) A compound of Formula (I) of (6), pharmaceutically acceptable salts or stereoisomers thereof:

wherein $R^1$ is selected from 6- or 7-membered nitrogen-containing fused heterocyclyl, 7- to 10-membered nitrogen-containing spiral heterocyclyl, any of which is optionally substituted with 1-3 substituent groups, and $R^1$ links to pyrimidine ring of Formula (I) via N atom, the substituent groups are selected from halogen atoms, cyano, amino, hydroxyl, $C_{1-4}$ alkyl, halo $C_{1-4}$ alkyl, hydroxyl $C_{1-4}$ alkyl, or $C_{1-4}$ alkoxy;

$R^1$ is further preferably selected from:

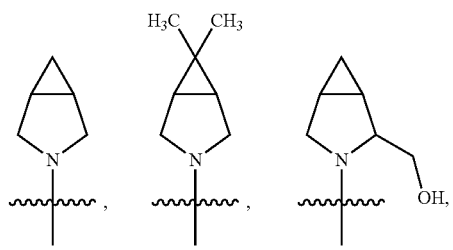

-continued

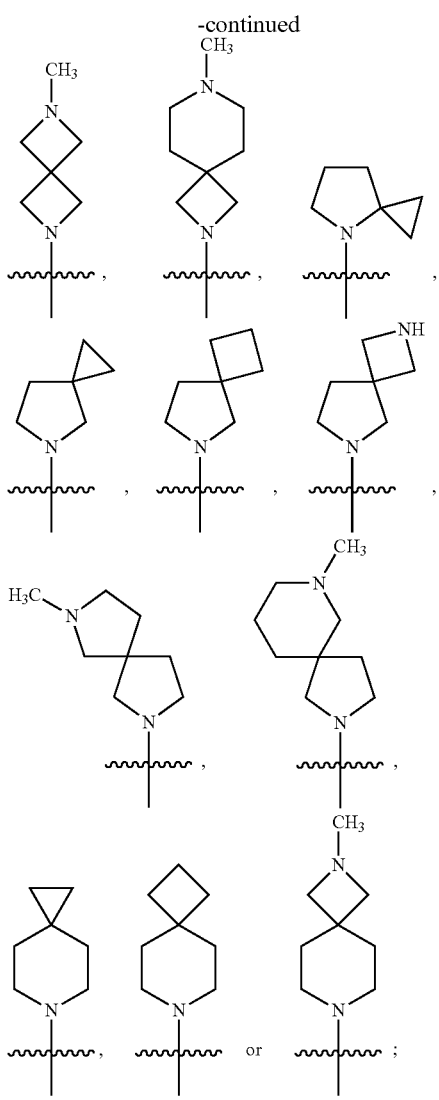

R[3] is preferably hydrogen; R[4] is preferably hydrogen;
m is preferably 0, 1 or 2; m is further preferably 0 or 1;
Z is preferably hydrogen, or sodium ion; Z is further preferably sodium ion;
R[5] represents -Q-R[7],
Q is selected from methylene or ethylene, and R[7] is selected from phenyl, pyrrolyl, furyl, pyridyl, thiazolyl, naphthyl, benzopyrrolyl, indenyl, quinolyl or indolyl, any of which is optionally substituted with 1-3 substituent groups,
the substituent groups are selected from halogen atoms, cyano, amino, hydroxyl, $C_{1-4}$ alkyl, halo $C_{1-4}$ alkyl, hydroxyl $C_{1-4}$ alkyl, or $C_{1-4}$ alkoxy.
R[5] is further preferably selected from:

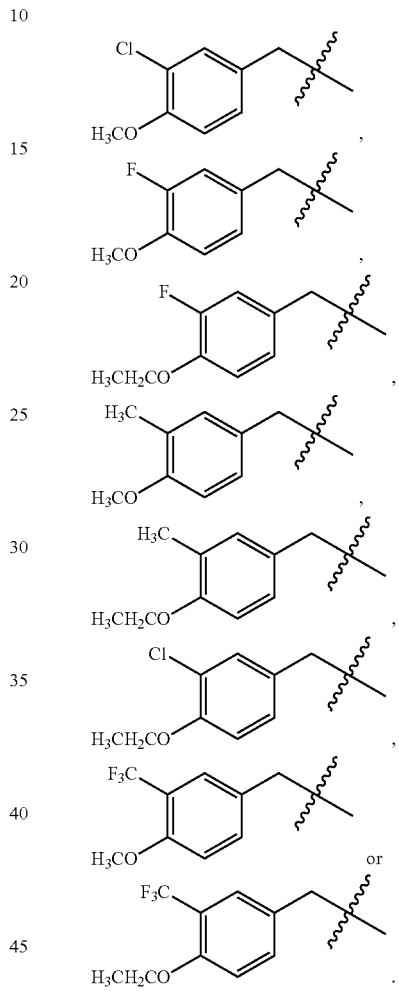

Specifically Preferred Compounds Include:

| Compound | Structural Formula |
|---|---|
| 1 | |

-continued
| Compound | Structural Formula |
|---|---|
| 2 | 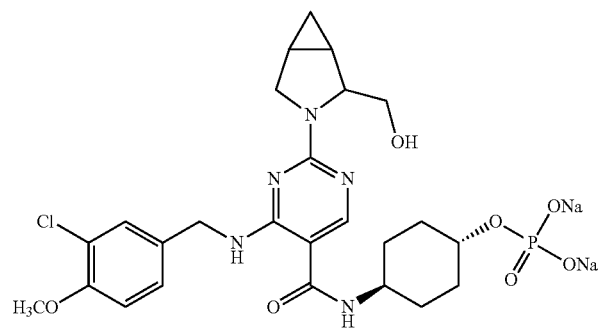 |
| 3 | 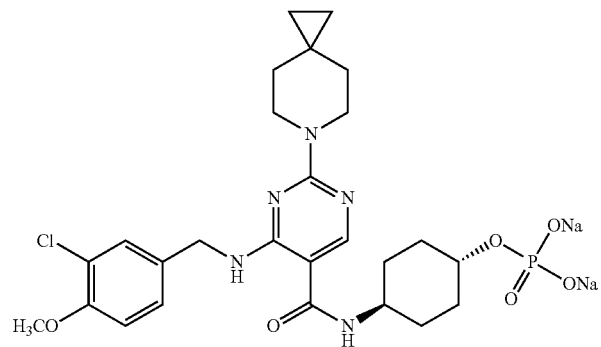 |
| 4 | 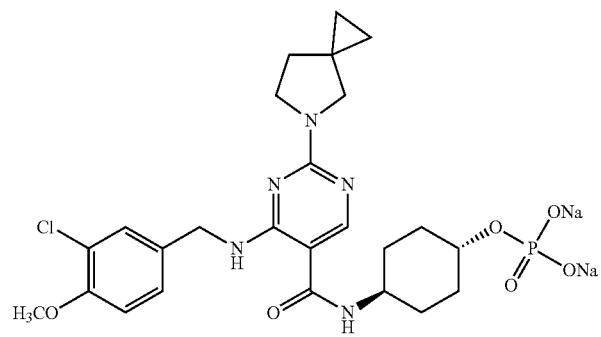 |
| 5 | 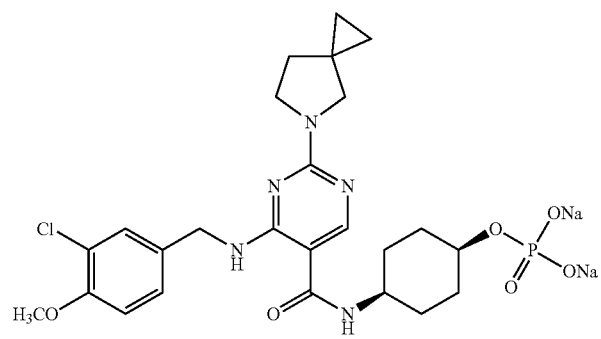 |

-continued
| Compound | Structural Formula |
|---|---|
| 6 | 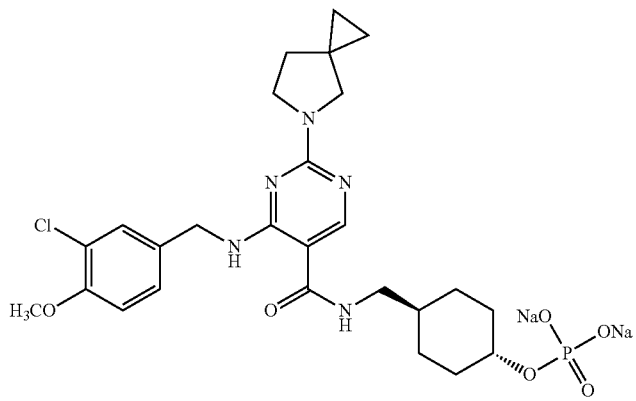 |
| 7 | 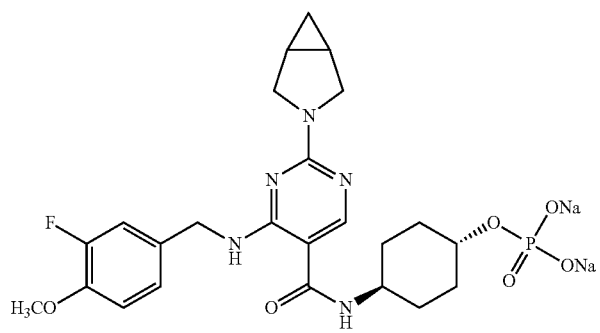 |
| 8 | 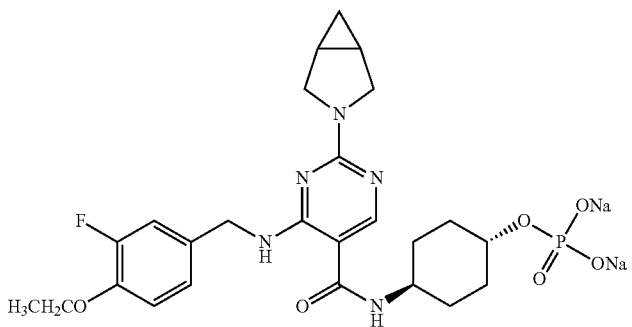 |
| 9 | 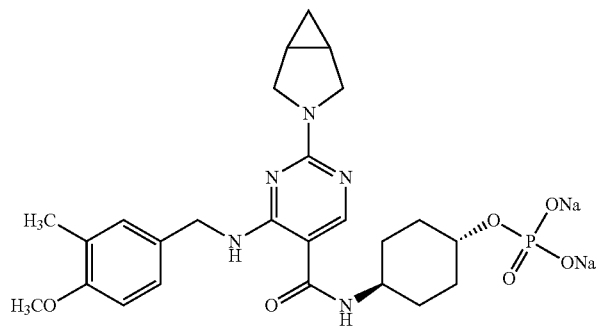 |

-continued
| Compound | Structural Formula |
|---|---|
| 10 | 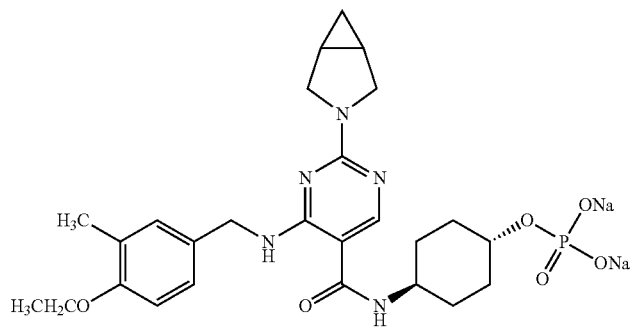 |
| 11 | 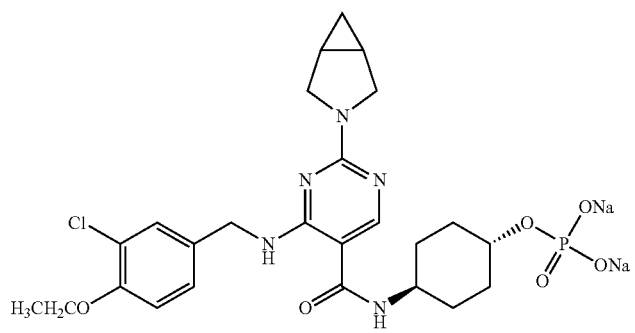 |
| 12 | 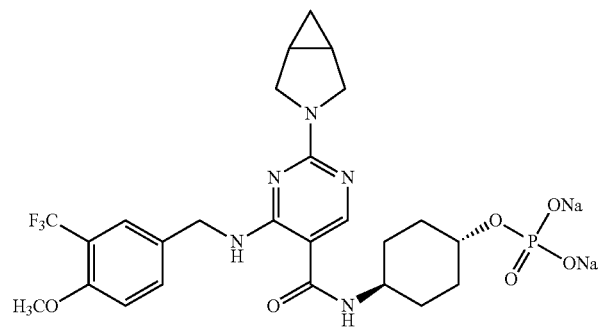 |
| 13 | 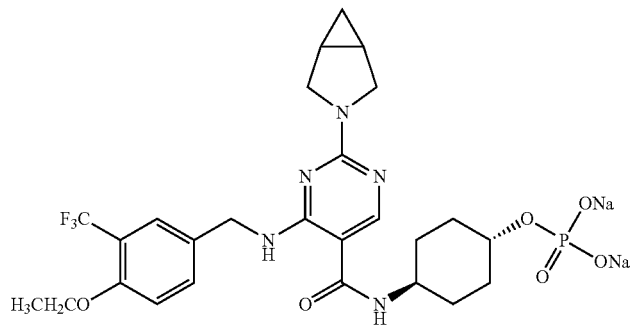 |

-continued
| Compound | Structural Formula |
|---|---|
| 1-1 | 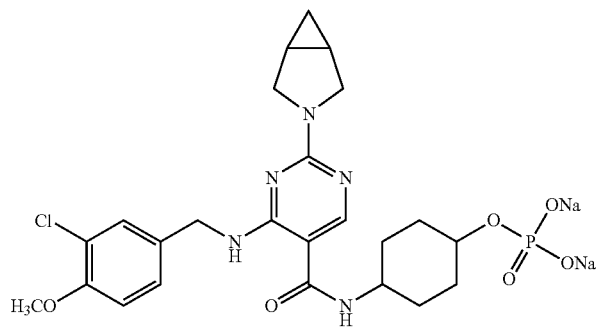 |
| 2-1 | 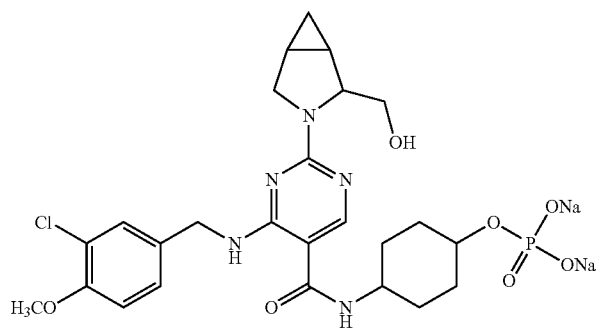 |
| 3-1 | 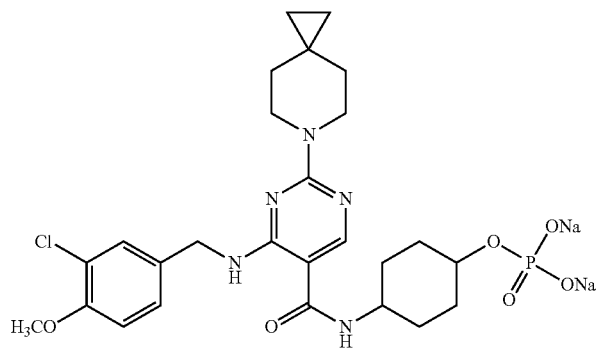 |
| 4-1 | 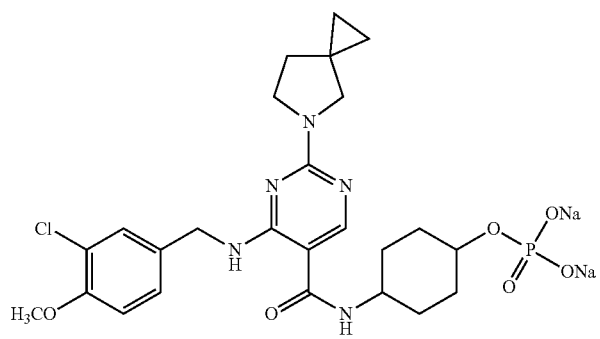 |

-continued
| Compound | Structural Formula |
|---|---|
| 5-1 | 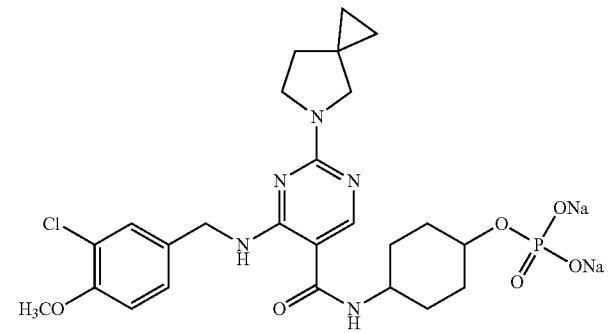 |
| 6-1 | 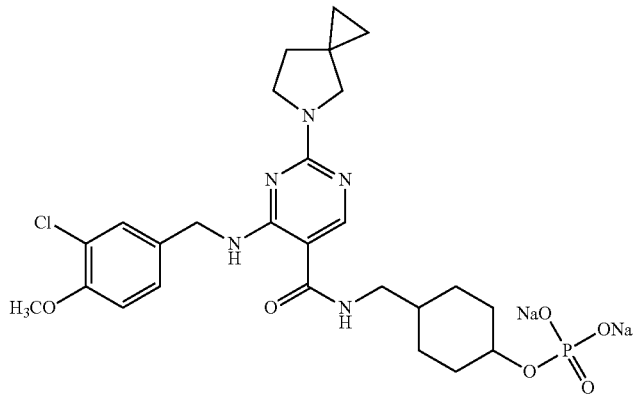 |
| 7-1 | 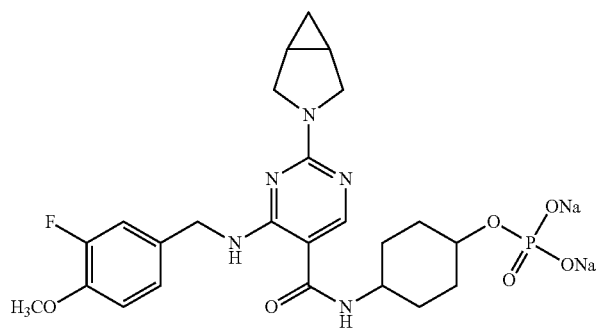 |
| 8-1 | 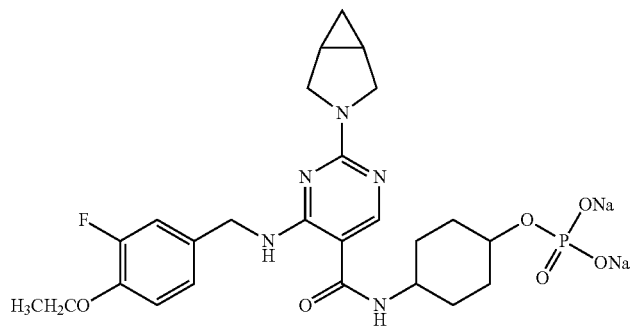 |

| Compound | Structural Formula |
|---|---|
| 9-1 | 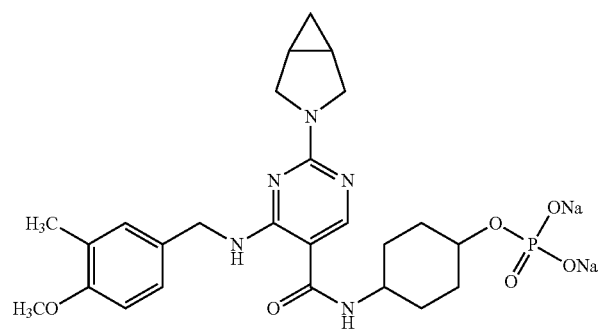 |
| 10-1 | 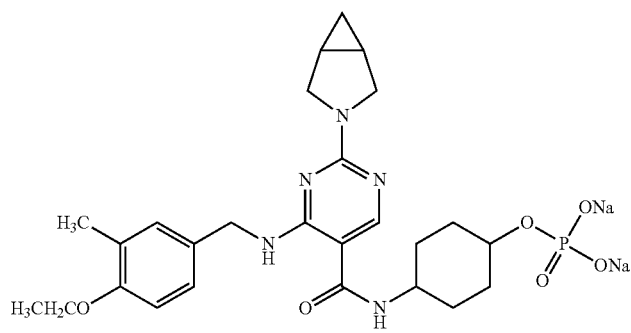 |
| 11-1 | 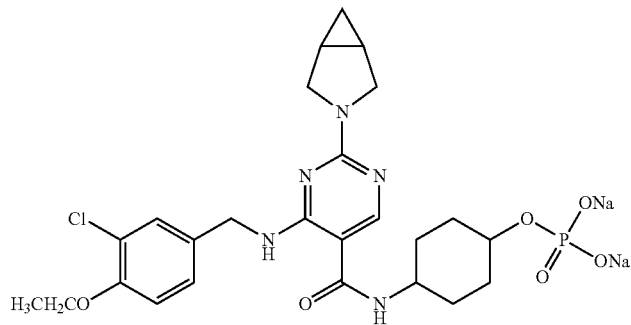 |
| 12-1 | 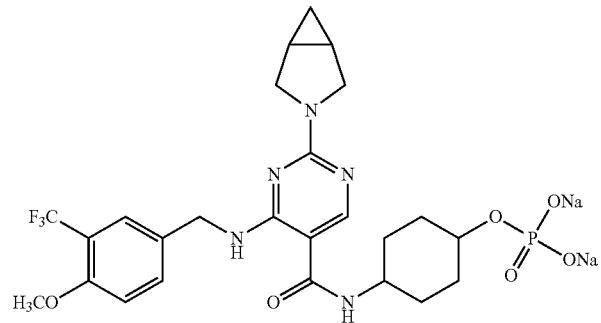 |

| Compound | Structural Formula |
|---|---|
| 13-1 | ![structure] |

In present invention, the term "halo" refers to being substituted with "halogen atom", and "halogen atom" refers to fluorine atom, chlorine atom, bromine atom, or iodine atom.

In the present invention, the term "$C_{1-6}$ alkyl" refers to straight or branched alkyl containing 1-6 atoms, such as methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc, in which $C_{1-4}$ alkyl is preferred. In the present invention, the term "$C_{1-4}$ alkyl" refers to the above examples containing 1-4 carbon atoms.

In the present invention, the term "$C_{1-6}$ alkylidene" refers to a straight or branched alkyl derivative from the above alkyl by removing one hydrogen atom, including —$(CH_2)_t$— (t is an integer from 1 to 6), for example, methylene, ethylene, propylidene etc, in which, $C_{1-4}$ alkylidene is preferred. In the present invention, the term "$C_{1-4}$ alkylidene" refers to the above examples containing 1-4 carbon atoms.

In the present invention, the term "$C_{1-6}$ alkoxy" refers to a group in which "$C_{1-6}$ alkyl" links to another structure via oxygen atom, for example, methoxy, ethoxy, propoxy, iso-propoxy, butoxy, iso-butoxy, tert-butoxy, sec-butoxy, penty-loxy, neo-pentyloxy, hexoxy, etc.

In the present invention, the term "halo $C_{1-6}$ alkyl" refers to the group derived from "$C_{1-6}$ alkyl" in which one or more hydrogen atoms are substituted by one or more "halogen atoms", and the terms "halogen atoms" and "$C_{1-6}$ alkyl" are as defined above.

In the present invention, the term "hydroxyl $C_{1-6}$ alkyl" refers to the group derived from "$C_{1-6}$ alkyl" in which one or more hydrogen atoms are substituted by one or more hydroxyl groups, and the term "$C_{1-6}$ alkyl" is as defined above.

In the present invention, the terms "carboxyl $C_{1-6}$ alkyl, $C_{1-6}$ alkylcarbonyl, $C_{1-6}$ alkoxycarbonyl, $C_{1-6}$ alkylamino, di($C_{1-6}$ alkyl)amino, $C_{1-6}$ alkylsulfonylamino" refer to groups which connect to another structure in the manner of HOOC—$C_{1-6}$ alkyl-, —$C_{1-6}$ alkyl-C(O)—, $C_{1-6}$ alkyl-O—C(O)—, $C_{1-6}$ alkyl-NH—, ($C_{1-6}$ alkyl)$_2$N—, $C_{1-6}$ alkyl-SO$_2$—NH—, respectively, in which "$C_{1-6}$ alkyl, $C_{1-6}$ alkylidene" are as defined above. Wherein carboxyl $C_{1-4}$ alkyl, $C_{1-4}$ alkylcarbonyl, $C_{1-4}$alkoxycarbonyl, $C_{1-4}$ alkylamino, di($C_{1-4}$ alkyl)amino, $C_{1-4}$ alkylsulfonylamino are preferred and the terms "carboxyl $C_{1-4}$ alkyl, $C_{1-4}$ alkylcarbonyl, $C_{1-4}$alkoxycarbonyl, $C_{1-4}$ alkylamino, di($C_{1-4}$ alkyl)amino, $C_{1-4}$ alkylsulfonylamino" refer to the above examples containing 1-4 carbon atoms, in which "$C_{1-4}$ alkyl, $C_{1-4}$ alkylidene" are as defined above.

In the present invention, "$C_{2-6}$ alkenyl" refers to a straight or branched or cyclic alkenyl containing at least one double bond and 2-6 carbon atoms, for example, ethenyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, cyclopentenyl, 1,3-cyclopentadienyl, cyclohexenyl, 1,4-cyclohexadienyl, etc.

In the present invention, "$C_{2-6}$ alkynyl" refers to a straight or branched alkynyl containing at least one triple bond and 2-6 carbon atoms, for example, ethynyl, propynyl, 2-butynyl, 2-pentynyl, 3-pentynyl, 4-methyl-2-pentynyl, 2-hexynyl, 3-hexynyl, 5-methyl-2-hexynyl, etc.

In the present invention, "6- to 7-membered nitrogen-containing fused heterocyclyl" refers to a kind of cyclic structure, including 6- to 7-membered saturated or partially saturated nitrogen-containing fused heterocyclyl, which contains 6-7 carbon atoms and/or heteroatoms and has at least two rings sharing two adjacent atoms, in which at least one of the heteroatoms is nitrogen atom, and examples of said "heteroatoms" include but are not limited to N, S, O, SO or SO$_2$. Specific examples include but are not limited to:

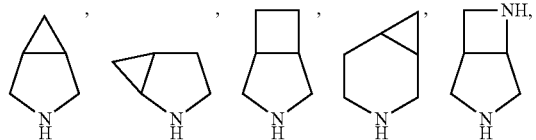

etc.

In the present invention, "7- to 12-membered nitrogen-containing spiral heterocyclyl" refers to a kind of cyclic structure which contains 7-12 carbon atoms and/or heteroatoms (at least one of the heteroatoms is nitrogen atom) and which is formed by at least two rings sharing one atom, in which examples of said "heteroatoms" include but are not limited to N, S, O, SO or SO$_2$. Specific examples include but are not limited to:

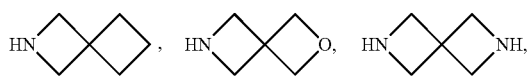

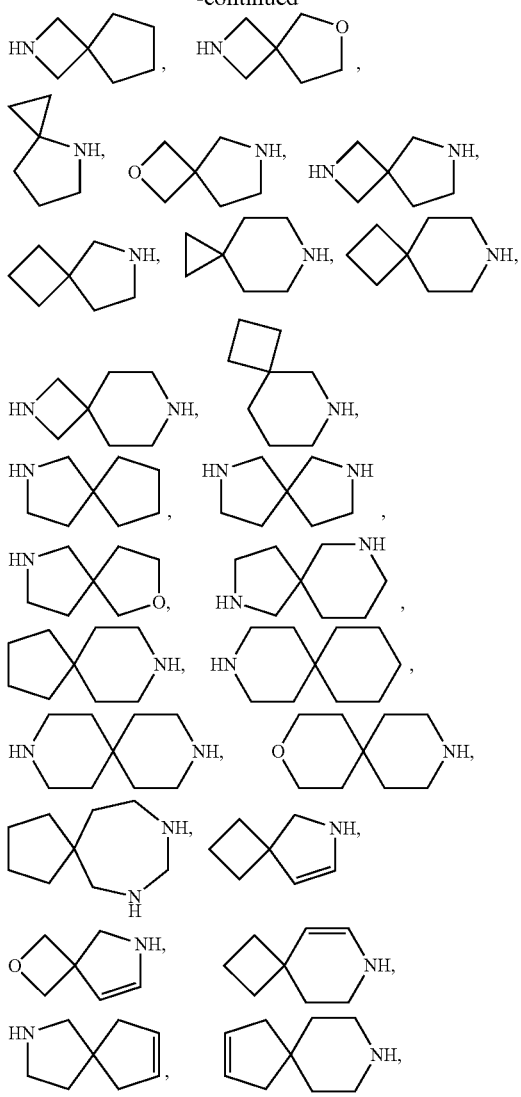

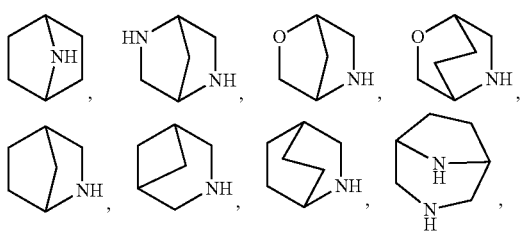

etc. Preferably, 7- to 10-membered nitrogen-containing spiral heterocyclyl refer to cyclic structure of the above examples containing 7-10 ring atoms.

In the present invention, "7- to 12-membered nitrogen-containing bridged heterocyclyl" refers to a kind of cyclic structure which contains 7-12 carbon atoms and/or heteroatoms (at least one of the heteroatoms is nitrogen atom) and which is formed by at least two rings sharing two atoms that are not adjacent to each other, in which examples of said "heteroatoms" include but are not limited to N, S, O, SO or SO$_2$. Specific examples include but are not limited to:

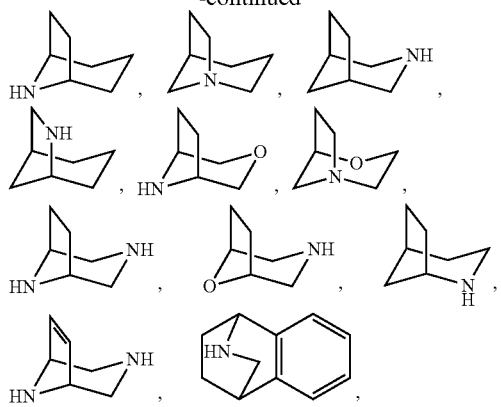

etc. Preferably, 7- to 8-membered nitrogen-containing bridged heterocyclyl refer to cyclic structure of the above examples containing 7-8 ring atoms.

In the present invention, "5- to 7-membered heterocyclyl" refers to a cyclic structure containing 5-7 ring atoms (including at least one heteroatom), in which examples of said "heteroatoms" include but are not limited to N, S, O, SO or SO$_2$. Specific examples include but are not limited to: tetrahydrofuryl, tetrahydrothienyl, tetrahydropyrrolyl, imidazolidinyl, pyrazolidinyl, piperidyl, morpholinyl, piperazinyl, 2-oxo-azacycloheptyl, 2-oxo-piperazinyl, dihydrothienyl, dihydropyrrolyl, dihydrooxazolyl, dihydropyrazolyl, furyl, thienyl, pyrrolyl, imidazolyl, pyrazolyl, thiazolyl, oxazolyl, pyrimidyl, pyridyl, pyrazinyl, tetrahydrooxazolyl, tetrahydroisooxazolyl, tetrahydrothiazolyl, 1,1-dioxo-isothiazolinyl, 4,5-dihydroimidazolyl, 1,2,3-triazolyl, 1,2,4-triazolyl, 2-pyridonyl, 4-pyridonyl, 1,2-diazacycloheptatrienyl, 1,3-diazacycloheptatrienyl, 1,4-diazacycloheptatrienyl, etc.

In the present invention, "8- to 10-membered fused cyclyl" refers to a kind of cyclic structure which contains 8-10 carbon atoms and/or heteroatoms and which is formed by at least two rings sharing two adjacent atoms, in which examples of the "heteroatoms" include but are not limited to N, S, O, SO or SO$_2$. Specific examples include but are not limited to:

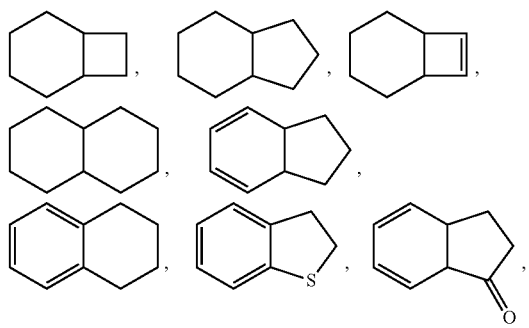

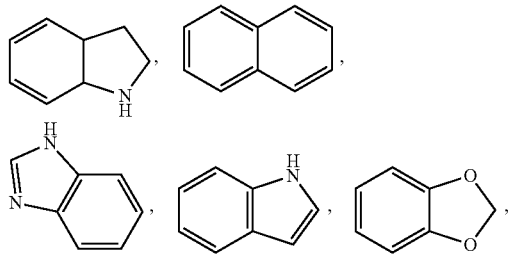

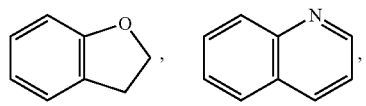
etc.

The term "6- to 14-membered aryl" refers to an aromatic group containing 6-14 carbon atoms, including 6- to 8-membered aryl and 8- to 14-membered fused aryl. The 6- to 8-membered aryl refers to a monocyclic aryl containing 6-8 carbon atoms, such as phenyl, cyclooctatetraenyl, etc. The 8- to 14-membered fused aryl refers to an aromatic unsaturated fused cyclic group containing 8-14 ring carbon atoms and formed by two or more rings sharing two adjacent atoms. Specific examples include but are not limited to naphthalene, anthracene, phenanthrene. The "6- to 10-membered aryl" refers to the cyclic structure containing 6-10 ring atoms within the above examples.

The above compounds of the present invention can be synthesized by the following methods and/or other methods known by an ordinary technician in the art, but not being limited to the following methods.

In the present invention, the meanings of abbreviations are shown as follows:

THF refers to tetrahydrofuran,

TLC refers to thin layer chromatography,

MTBE refers to methyl tert-butyl ether,

DMF refers to N,N-dimethylformamide,

DIEA refers to N,N-diisopropylethylamine,

HATU refers to 2-(7-azabenzotriazol-1-yl)-N,N,N',N'-tetramethyluronium hexafluorophosphate.

Reaction Scheme:

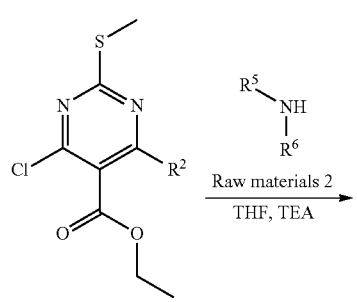

Raw materials 1

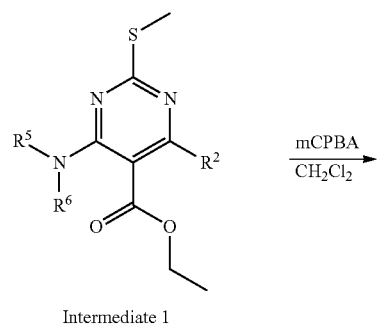

Intermediate 1

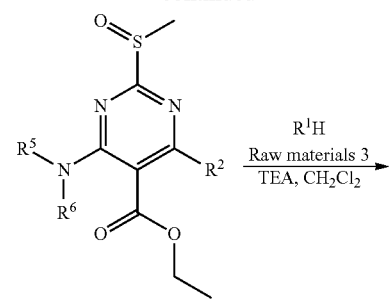

Intermediate 2

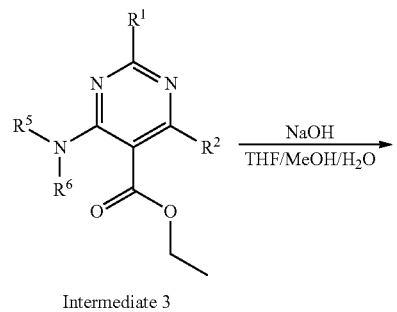

Intermediate 3

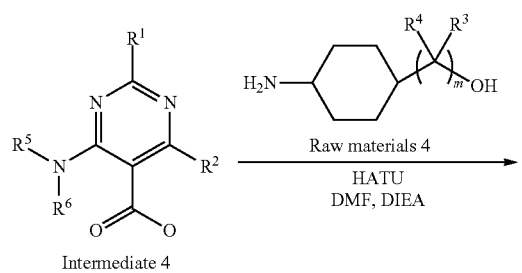

Intermediate 4

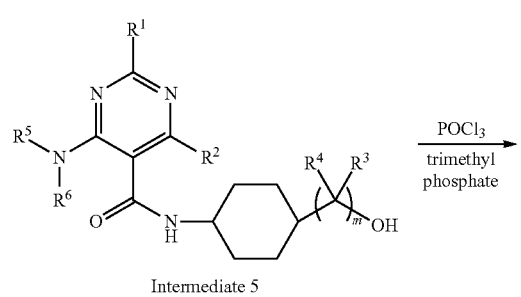

Intermediate 5

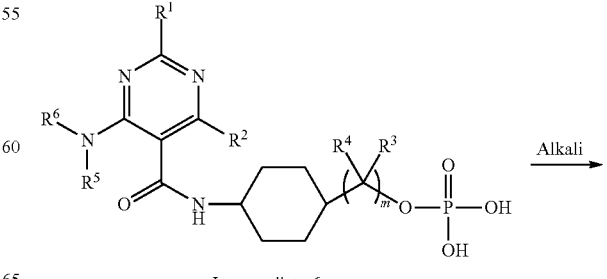

Intermediate 6

-continued

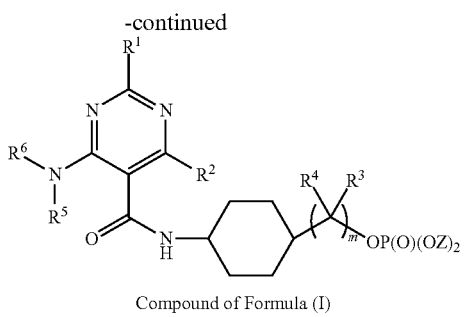

Compound of Formula (I)

Reaction Steps

Step 1: Synthesis of Intermediate 1

Raw material 2 is dissolved in an organic solvent, an organic alkali is added dropwise, stirred at room temperature, raw material 1 is added under ice-bath condition. The reaction is stirred at room temperature until the end of reaction, and evaporated at reduced pressure to remove solvent. A certain amount of ethyl acetate and water are added for extraction, the resultant organic layer is dried and evaporated at reduced pressure to remove solvent until an oily substance is obtained. A certain amount of organic solvent (e.g., methanol) is added, solid is precipitated and vacuum filtered, the resultant filter cake is vacuum dried to obtain Intermediate 1. The organic solvent is preferably methanol, DCM or THF, further preferably THF, and the organic alkali is preferably triethylamine.

Step 2: Synthesis of Intermediate 2

Intermediate 1 is dissolved in an organic solvent, m-chloroperoxybenzoic acid (mCPBA) in dichloromethane solution is added dropwise under ice-bath condition. The reaction is conducted at room temperature and quenched by adding a saturated inorganic alkali solution. After extraction, organic phase is washed with saturated inorganic alkali solution, saturated sodium chloride aqueous solution, respectively. The organic layer is dried (dried over anhydrous sodium sulfate), filtered to obtain Intermediate 2 which is directly used in next reaction without purification. The organic solvent is preferably dichloromethane, and the saturated inorganic alkali solution is preferably saturated sodium bicarbonate solution.

Step 3: Synthesis of Intermediate 3

Raw material 3 is added to Intermediate 2 under stirring condition, and an organic alkali is added dropwise under ice-bath. The reaction is conducted at room temperature and quenched by adding a saturated inorganic alkali solution, then extracted, dried and concentrated to obtain an oily substance. The oily substance is dissolved in organic solvent, stirred and vacuum filtered to obtain Intermediate 3. The organic solvent is preferably methanol, the organic alkali is preferably triethylamine, and the saturated inorganic alkali solution is preferably saturated ammonium chloride solution.

Step 4: Synthesis of Intermediate 4

Intermediate 3 is dissolved in an organic solvent, an inorganic alkali solution is added. The solution is refluxed until the end of reaction, and then cooled to room temperature. An inorganic acid (e.g., hydrochloric acid) is added to regulate pH=3 to precipitate solid. After solvent is removed, water is added to and stirred, filtered, vacuum dried to obtain Intermediate 4. The organic solvent is preferably methanol, tetrahydrofuran or a mixture solvent of tetrahydrofuran and methanol, further preferably a mixture solvent of tetrahydrofuran and methanol, the inorganic alkali solution is preferably sodium hydroxide solution.

Step 5: Synthesis of Intermediate 5

Intermediate 4 is dissolved in an organic solvent, an organic alkali is added dropwise under ice-bath, then HATU is added, Raw Material 4 is added under stirring. The reaction is stirred at room temperature until the end of reaction, water is added to precipitate solid. After suction filtration, filter cake is washed with water, air-dried, then recrystallized with acetone to obtain Intermediate 5. The organic solvent is preferably DME and the organic alkali solution is preferably DIEA.

Step 6: Synthesis of Intermediate 6

Intermediate 5 is dissolved in an organic solvent, POCl$_3$ is added dropwise under ice-bath. The reaction is stirred at room temperature until the end of reaction. The reaction liquid is cooled under ice-bath, an inorganci alkali solution is added to generate solid. After filtration, the solid is purified by preparative chromatography to obtain Intermediate 6. The organic solvent is preferably trimethyl phosphate, the inorganic alkali solution is preferably NaHCO$_3$ solution.

Step 6: Synthesis of Compound of Formula (I)

Intermediate 6 is dissolved in an organic solvent, an alkali solution is added dropwise under ice-bath, the reaction is stirred until the generation of an insoluble substance. After filtration, solid is washed with a small amount of water and acetone to obtain a white solid as the compound of Formula (I). The organic solvent is preferably methanol, the alkali solution is preferably sodium hydroxide solution, NaHCO$_3$ solution or Na$_2$CO$_3$ solution.

Wherein Raw material 2=$R^5R^6N$, Raw material 3=$R^1H$, and in the Reaction Scheme above, $R^1$, $R^2$, $R^3$, $R^4$, $R^5$, $R^6$ and Z are as defined above.

The present invention seeks to protect "pharmaceutically acceptable salts" of compounds of Formula (I), which includes alkali metal salts, such as sodium salts, potassium salts, lithium salts, etc. Alkaline earth metal salts, such as calcium salts, magnesium salts, etc. Other metal salts, such as aluminum salts, iron salts, zinc salts, copper salts, nickel salts, cobalt salts, etc. Inorganic alkali salts, such as ammonium salts; Organic alkali salts, such as tert-octylamine salts, dibenzylamine salts, morpholine salts, glucosamine salts, phenylglycine alkyl ester salts, ethanediamine salts, N-methylglucosamine salts, guanidine salts, diethylamine salts, triethylamine salts, dicyclohexylamine salts, N,N'-dibenzylethanediamine salts, chloroprocaine salts, procaine salts, diethanol amine salts, N-benzyl-phenylethylamine salts, piperazine salts, tetramethylammonium salts, tri(hydroxymethyl)methylammonium salts, etc. Haloid acid salts, such as hydrofluorides, hydrochlorides, hydrobromides, hydriodides, etc. Inorganic acid salts, such as nitrates, perchlorates, sulfates, phosphates, etc. Low-alkyl sulfonates, such as, methylsulfonates, trifluoromethylsulfonates, ethyl-sulfonates, etc. Arylsulfonates, such as benzenesulfonates, p-benzenesulfonates, etc. Organic acid salts, such as acetates, malates, fumarates, succinates, citrates, tartrates, oxalates, maleates, etc. Amino acid salts, such as glycine salts, trimethylglycine salts, arginine salts, ornithine salts, glutamine salts, aspartates, etc.

In the present invention, the "stereoisomers" of compounds of Formula (I) may drop comprise conformational isomers and configurational isomers, while configurational isomers further comprise cis-trans-isomers and optical isomers. The "stereoisomers" means that when the compound of the present invention contains one or more asymmetric centers, each of them generates two optical isomers. The scope of the present invention covers all possible optical isomers, mixtures of diastereoisomers and pure or partially pure compounds. When a compound of the present invention contains an olefinic double bond, unless specifically stated, the present invention comprises cis-isomer and trans-isomer thereof. Any compound of the present invention may be present in tautomeric form, which has different hydrogen link-points caused by shift of one or more double bonds. For example, a ketone and its enol are ketone-enol tautomers. All of tautomers and mixtures thereof are in the scope of the present invention.

In the present invention, "prodrug or pro-drug" refers to an ester of the active compound formed with an organic acid or inorganic acid when the compound has a group, such as hydroxyl-capable of forming an ester. The above prodrug can further react with an inorganic alkali or organic alkali to form a salt, which is also defined as "prodrug". "Produrg" may be helpful in improving problems of physical and chemical properties of the active compound such as solubility. The prodrug is stable in water or acid solution, and is transferred into free active compound by dissociation under enzymatic or non-enzymatic conditions so as to exert pharmacological action. The active compound is also called as "original drug". Prodrug has better solubility, is easy to be absorbed by animal body or human body, and quickly converts into original active compound in blood to exert pharmacological action.

The compounds of Formula (I), pharmaceutically acceptable salts, esters and stereoisomers can be used in mammal such as human via oral, parenteral (intravenous, intramuscular, subcutaneous or endorectal), intrapulmonary or topical administration, etc. The content of the compounds of the present invention in a pharmaceutical preparation is 1% to about 100% by weight relative to single preparation. The dosage varies in accordance with the subject to be administrated, administration routes, diseases and symptoms. For example, a compound of the present invention (used as active ingredient) can be orally administrated to a diabetic patient (with body weight of about 60 kg) in a following dose: about 0.01 to 1000 mg per day, preferably 5 to 500 mg per day, more preferably 50 to 300 mg per day. This dose can be administrated once in single dose or in batches for several times per day.

The compounds of Formula (I) of the present invention, pharmaceutically acceptable salts or stereoisomers thereof can constitute pharmaceutical compositions with one or more pharmaceutically acceptable carriers. Said pharmaceutical compositions can be made into clinically conventional pharmaceutical preparations, which can be applied to a patient in need of such treatment via oral or parenteral administration. The preparations can be, for example, tablets, granules, capsules, powders, injections, inhalations, preparations for sublingual administration, syrups, gels, ointments, suppositories, lotions, nasal drops, sprays, transdermal preparations, etc. These preparations can be prepared via conventional methods, by adding pharmaceutically acceptable carriers such as excipients, binding agents, humidifiers, disintegrating agents, thickening agents, etc.

The compounds of Formula (I) of the present invention or pharmaceutically acceptable salts or stereoisomers thereof can be prepared into a pharmaceutical composition together with one or more second therapeutically active agents, in which the therapeutically active agents are selected from vasodilators, prostaglandin E1, prostacyclin, α-adrenergic receptor retardants, mixed α,β-blockers, α-blockers, 5α-reductase inhibitors, α2-adrenergic receptor retardants, ACE inhibitors, NEP inhibitors, central dopamine agents, vasoactive intestinal peptide, calcium channel blockers, thiazines, or mixtures thereof.

The compounds of Formula (I) of the present invention or their pharmaceutically acceptable salts or stereoisomers have better activity of inhibiting PDE-5 (phosphodiesterase-5), can thus be used for manufacturing a medicament for treatment and/or prophylaxis of diseases caused by cGMP signal transduction dysfunction such as sexual dysfunction and lower urinary tract symptoms.

The beneficial effects of the compounds of the present invention are further illustrated by the following in vivo pharmacokinetic experiments, in vitro experiments for determination of pharmacological activity and solubility experiments. However, it should not be interpreted as admission that the compounds of the present invention only have the following beneficial effects.

Description: The molecular structural feature of the compounds of the present invention is characterized by phosphate based disodium salt, which can be hydrolyzed under certain pH condition to form alcohol structure. For example, Compound 1 of the present invention can generate original active Compound Q after hydrolytic deacidification, and the specific structure of Compound Q is as follows:

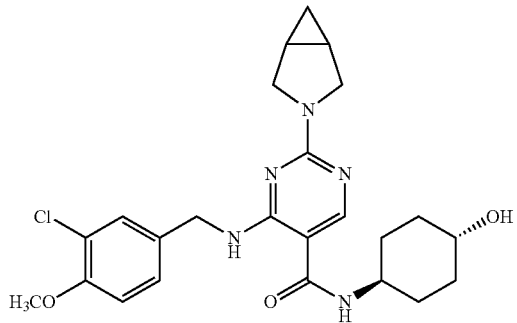 [SMILES: COc1ccc(CNc2nc(N3CC4CC4C3)ncc2C(=O)N[C@H]2CC[C@H](O)CC2)cc1Cl]

Compound Q is an "original drug" of the compound of the present invention. The prodrug has high solubility in water, and changes into "original drug" after metabolism in vivo. The prodrug can be inactive when administered to a patient, but can be converted into active compound in vivo. When the compounds of Formula (I) has hydroxyl groups, they can form ester type prodrugs with amino acids, phosphoric acid, etc.

Experiment 1

Determination of In Vivo Pharmacokinetics of the Compounds of the Present Invention (Intravenous Injection, Oral Administration)

1. Design of Experiment

| Anima number | Gender | Body weight | Administration route | Time point for blood collection | Type of biological sample |
|---|---|---|---|---|---|
| 3 | Male | 220-240 g | Intragastric administration (PO) | 0.17 h, 0.5 h, 1 h, 2 h, 4 h, 6 h, 8 h, 24 h | Plasma |
| 3 | Male | | Intravenous injection (IV) | 0.083 h, 0.25 h, 0.5 h, 1 h, 2 h, 4 h, 6 h, 8 h, 24 h | |

2. Test Samples

Some of the compounds of the present invention were prepared according to the methods in the examples and were dissolved in physiological saline solution. Avanafil with structure given as above was purchased from market, used as internal standard and dissolved with methanol.

3. Apparatus

Instrument and equipment: API4000 LC-MS/MS
Chromatographic column: Agilent XDBC$_{18}$(2.1×50 mm, 5 μm)

4. Blood Collection

Rat blood collection: animal was fixed, heated at tail with water-bath 10 min before each time point, about 200 μL of blood was collected from caudal vein, and the collected blood was placed in anticoagulative tube containing heparin sodium. Blood sample was centrifuged under 8000 rpm at 4° C. for 6 min to obtain plasma sample, and the plasma must be prepared within 30 min after blood collection. The plasma was stored in −80° C. refrigerator before test.

5. Experimental Method

1) Take a sample to be tested from refrigerator (−80° C.), melt in situ at room temperature, then eddy for 5 min;
2) Precisely move 20 μL of sample into 1.5 mL centrifuge tube;
3) Add 200 μL of internal standard solution;
4) Eddy for 3 min, then centrifuge for 5 min (12000 rpm);
5) Precisely move 50 μL of supernatant and add into 150 μL of water, eddy for 3 min, and load to LC-MS/MS for analysis.

6. Tracking Detection

TABLE 1

Concentration of Compound 1 in rat body after intravenous injection (IV: 1 mg/kg)

| Time (h) | Rat 1 | Rat 2 | Rat 3 | Mean | SD | RSD % |
|---|---|---|---|---|---|---|
| | | | Concentration (ng/mL) | | | |
| 0.083 | 162 | 183 | 151 | 165.33 | 16.26 | 0.10 |

At time point of 0.083 h, the concentration of prodrug Compound 1 was 165.33 ng/mL, which was less than the concentration of original drug Compound Q of 1104 ng/mL. Almost all of the prodrug Compound 1 was converted into the original drug Compound Q at this time point. Compound 1 of the present invention was the prodrug of Compound Q. After intravenous injection of (IV), the plasma concentration of Compound 1 could only be detected at time point of 0.083 h by LC-MS/MS, and Compound 1 could not be detected in plasma at all other time points, but the plasma concentration of Compound Q could be detected after 0.083 h, which showed that the prodrug Compound 1 was quickly converted into original drug Compound Q (within 0.083 h) in rats. Compound 1 was not detected in plasma by LC-MS/MS at each of time points after intragastric administration (PO), but the original drug Compound Q was detected, which showed that the prodrug Compound 1 was immediately converted into the original drug Compound Q after entering stomach. It is thus confirmed that Compound 1 of the present invention was completely converted into the original Compound Q after intravenous injection and intragastric administration. Hence, the experimental results of Compound 1 in this experiment were presented by tracking detection of plasma concentration of the original drug Compound Q.

7. Data Processing Method

Test sample (plasma sample) concentrations were output by using Analyst 1.5.1 of AB Company. Parameters. Mean values, standard deviation and variable coefficient (those directly outputed by Analyst 1.5.1 were not calculated), were calculated by Microsoft Excel. PK parameter was calculated by using software Pharsight Phoenix 6.2.

TABLE 2

Evaluation results of PK of Compound 1 in rats after intravenous injection via detecting Compound Q (IV: 1 mg/kg)

| Test substance | $T_{1/2}$ (h) | $AUC_{inf}$ (h*ng/mL) | $CL_{\_obs}$ (L/h/kg) | $Vss_{\_obs}$ (L/kg) |
|---|---|---|---|---|
| Avanafil | 0.5 | 382 | 5.3 | 3.6 |
| Compound 1 (data of detecting Compound Q as converted from Compound 1) | 4.0 | 1104 | 0.91 | 3.8 |
| Compound Q | 2.40 | 858 | 1.18 | 3.44 |

TABLE 3

Evaluation results of PK of Compound 1 in rats after intragastric administration via detecting Compound Q (PO: 1 mg/kg)

| Test substance | $T_{1/2}$ (h) | $AUC_{inf}$ (h*ng/mL) | $C_{max}$ (ng/mL) | $T_{max}$ (h) | F % |
|---|---|---|---|---|---|
| Avanafil | 0.5 | 49.8 | 18.3 | 0.25 | 4.5 |
| Compound 1 (data of detecting Compound Q as converted from Compound 1) | 3.7 | 595 | 86.1 | 2 | 54 |
| Compound Q | 2.03 | 604 | 133 | 1 | 70.4 |

TABLE 4

Evaluation results of PK in rats after intravenous injection via detecting Compounds 4-A, 9-B

| Test substance | Dose (mg/kg) | $T_{1/2}$ (h) | $AUC_{inf}$ (h*ng/mL) | $Cl_{\_obs}$ (L/h/kg) | $Vss_{\_obs}$ (L/kg) |
|---|---|---|---|---|---|
| Avanafil | 2 | 0.53 | 382 | 5.31 | 3.56 |
| Compound 4-A | 1 | 3.50 | 1033 | 1.01 | 4.47 |
| Compound 9-B | 2 | 4.1 | 2582 | 0.78 | 4.48 |

TABLE 5

Evaluation results of PK in rats after intragastric administration via detecting Compounds 4-A, 9-B

| Test substance | Dose (mg/kg) | $T_{1/2}$ (h) | $AUC_{inf}$ (h*ng/mL) | $C_{max}$ (ng/mL) | $T_{max}$ (h) | F % |
|---|---|---|---|---|---|---|
| Avanafil | 2 | 0.51 | 50 | 18 | 0.33 | 4.5 |
| Compound 4-A | 2 | 2.11 | 704 | 124 | 6.0 | 35 |
| Compound 9-B | 5 | 5.4 | 4718 | 377 | 6 | 65 |

Wherein $T_{1/2}$ represents half-life period; $AUC_{inf}$ represents area under drug-time curve 0→∞; CL represents clearance rate; Vss represents apparent volume of distribution; $C_{max}$ represents peak concentration of the compound in plasma; $T_{max}$ represents the time at which the compound reached the peak concentration; F % represents absolute bioavailability.

Experimental Conclusions

It was shown in Tables 1, 2 and 3 that the prodrug Compound 1 was almost completely converted into the original drug Compound Q which indeed exerted pharmacological activity in rats, and both of Compound 1 and Compound Q of the present invention showed good pharmacokinetic features. After administration of Compound 1 in rats, the detected pharmacokinetic features of Compound Q were similar to that of Compound Q as administrated alone, such as clearance rate, AUC, etc. It showed that Compound 1 was converted into its original drug Compound Q in rats, the pharmacological activity was exerted by Compound Q, and the prodrug Compound 1 prepared by Compound Q did not affect the intrinsic pharmacological activity of the compound Q. Thus, the compound 1 of the present invention has good inhibition effects on sexual dysfunction caused by abnormal expression of PDE-5 signal pathway.

It was shown in Tables 1, 2 and 3 that the prodrug Compound 1 was almost completely converted into the original drug Compound Q which indeed exerted pharmacological activity in rats. In comparison with Avanafil, the compound of the present invention in rats possessed longer half-life periods and duration time of pharmacological activity, increased exposure dose and bioavailability after IV and PO administration. From Tables 4 and 5, it could be seen that the prodrug Compounds 4 and 9, detected by the original drugs Compounds 4-A and 9-B, showed superior PK parameters relative to Avanafil in terms of half-life, exposure dose, duration time of pharmacological activity and bioavailability in rats. Thus, the compounds of the present invention had better druggability, especially, the oral bioavailability of the compound of the present invention was significantly elevated in comparison with Avanafil, so the compounds of the present invention were more prospective in clinical application.

Experiment 2

Determination of In Vitro Pharmacological Activity of Compound Q

Test Sample:
Compound Q, with structure given as above was prepared according to steps 1-8 of Example 1; Avanafil was purchased from market, of which the structure was given above.

Experimental Method:
Enzyme assay, Caliper Mobility-Shift PDE-5A Assay:
Test sample was precisely weighed, dissolved in DMSO, sufficiently mixed, to obtain 10 mM solution. The mother liquor was then diluted with DMSO to a concentration of 0.5 mM, and continuously diluted by 3.162 times in gradient manner to obtain 11 concentrations in total.

To a 96-well plate was added 20 μL of 10 μM FL-cGMP substrate in (buffer was diluted from 2 mM to 10 μM), 1 μL solution of DMSO solution with compound or DMSO solution without compound, then 29 μL of 1.38 ng/μL PDE-5A enzyme buffer (the buffer was diluted from 100 ng/μL to 1.38 ng/μL), the maximum final concentration of compound was 10 μM. After incubation at 30° C. for 1 h, 20 μL of 70 μM EDTA was added to terminate reaction. 26 μL of reaction liquid of each well was transferred to a 384-well plate, detected with EZ reader II. Inhibition rate was calculated by the following formula, and $IC_{50}$ value was calculated from inhibition rate by using Prism 5.0.

Inhibition rate=[conversion rate (ZPE)−conversion rate (sample)]×100/[conversion rate (ZPE)−conversion rate (HPE)]

Notation: HPE: blank control without enzyme; ZPE: blank control without compound.

Preparation of Buffer Solution:

| Ingredient | MW | 200 mL |
|---|---|---|
| HEPES (pH 7.5) | 238.3 | 4.8 grams |
| 1M $MgCl_2$ solution | | 1 mL |
| 30% Brij35 | | 13.2 μL |

The above ingredients were dissolved, regulated with 1M NaOH to pH 7.5, diluted to constant volume of 200 mL, and stored at 4° C.

Experimental Results and Conclusions

TABLE 6

$IC_{50}$ values of the compounds on PDE-5A

| Compound | PDE-5A (nM) |
|---|---|
| Compound Q | 4.02 |
| Avanafil | 17.32 |

Conclusions: It can be seen from Table 6, Compound Q had good inhibition activity on PDE-5A. When Compound Q was prepared into its prodrug Compound 1, Compound 1 could exert effects in vivo via Compound Q, and its pharmacological activity was not affected.

Experiment 3

Determination of In Vitro Pharmacological Activity of Compound Q

Test Sample:
Compound Q, with structure defined as above, was prepared according to Steps 1-8 of Example 1; Avanafil was purchased from market, of which the structure was defined above.

Experimental Method

Enzyme Assay

Scintillation counter (Topcount, Packard) PDE-5assay: PDE-5 source, human platelets Test sample was precisely weighed, dissolved into DMSO, sufficiently mixed to prepare a concentration of 10 mM stock solution, diluted by half-log (3.162 times) to obtain 8 concentrations.

Compound or solvent was preincubated with 35 μg/mL enzyme solution (dissolved in Tris-HCl buffer solution, pH7.5) for 15 min at 25° C., then 1 μM cGMP and 0.01 μM [$^3$H] cGMP were added to start reaction. After incubation for 20 min, the reaction was terminated at 100° C., snake venom nucleotidase was added to convert the product [$^3$H] cGMP into [$^3$H] Guanosine, which was separated by AG1-X2 resin, and the amount of generated [$^3$H] Guanosine was counted. The maximum concentration of compounds involved in reaction were 1 μM.

Compound was added to substrate-containing (1.01 μM [3H]cGMP+cGMP) buffer solution 50 mM Tris-HCl, pH 7.5, 5 mM MgCl$_2$, incubated at 25° C. for 15 min, enzyme PDE-5 was added, the mixture was incubated at 25° C. for 20 min, and the product [3H]Guanosine was quantitatively determined. The maximum concentration of compounds involved in reaction were 1 μM.

IC$_{50}$ values were calculated by software MathIQ™ (ID Business Solutions Ltd., UK).

TABLE 7

IC$_{50}$ values of the compound to PDE-5

| Compound | PDE-5 (nM) |
| --- | --- |
| Compound Q | 1.31 |
| Compound 4-A | 0.80 |
| Compound 9-B | 7.72 |
| Avanafil | 3.10 |

Experimental Conclusions it was shown in Table 7 that Compound Q had good inhibition activity on PDE-5 enzyme, which is equivalent to the inhibition activity of control drug, and could be used in the treatment of diseases related with PDE-5 enzyme, especially diseases or disorders mediated by PDE-5 enzyme. It had remarkable clinical significance. Thus, the prodrug Compound 1 had the same inhibition activity on PDE-5 enzyme.

Experiment 4

Comparison Test of Solubility of Compound 1 and Compound Q

Test Sample:

Compound 1 (prepared according to the method of Example 1) and Compound Q of the present invention.

Experimental Method:

1. Method for preparing sample of Compound 1, 6 parts of test sample were precisely weighed, each was 2 mg and was separately added to 40 μL of buffer solutions of pH 4, pH 5, pH 6, pH 7, pH 8, pH 9, respectively. Jolted (ultrasonic treatment for 5 min) and detected by visual observation.

2. Method for preparing sample of Compound Q, 4 parts of test sample were precisely weighed, each was 1 mg and was separately added to 1 mL of buffer solutions of pH 3, pH 5, pH 7, pH 9, treated with ultrasound for 5 min and filtered through 0.45 μm organic filtration membrane. The filter liquors were used as test sample solutions. 10 μL of each was injected into high performance liquid chromatograph, and peak areas were recorded.

Control solution of compound Q:

4.88 mg of test sample was precisely weighed, placed in 10 mL volumetric flask, added to 1 mL of methanol for dissolution, then diluted with methanol to constant volume to obtain a solution containing 0.488 mg of control per 1 mL, which was used as mother liquor A. The mother liquor A was gradually diluted with methanol to obtain control solutions containing 0.0488 mg or 0.00976 mg per 1 mL.

Linear regression was performed by using control concentration (C) as abscissa, and peak area (Y) as ordinate so as to obtain a linear equation. The concentrations of test sample solutions were obtained by putting the peak areas of test sample solutions into the linear equation.

The control linear equation of Compound Q is: Y=24262C, correlation coefficient r=1.0000.

3. Apparatus:

Instrument and equipment: Agilent 1200 HPLC

Chromatography column: YMC-Pack-Pro C$_{18}$(150×4.6 mm, 5 μm)

Electronic scale: Sartorius CPA225D

4. Analysis Conditions:

Buffer solution: 0.02 mol/L ammonium dihydrogen phosphate (added 0.2% triethylamine, and regulated with phosphoric acid to pH=6.0)

Phase A: acetonitrile-buffer solution=10:9, Phase B: acetonitrile-buffer solution=80:20

Mobile phase: Phase A: Phase B=65:35

Flow rate: 1 mL/min

Detection wavelength: 254 nm Sample size: 10 μL

5. Preparation of buffer solution:

1) pH4.0 hydrochloric acid/potassium hydrogen phthalate solution:

1.02 g of potassium hydrogen phthalate was weighed, added to 0.05 mL of 0.2 mol/L hydrochloric acid solution and an appropriate amount of water for dissolution, diluted by adding water to 100 mL, mixed homogeneously to obtain the subject solution.

2) pH5.0 sodium hydroxide/potassium hydrogen phthalate solution 1.02 g of potassium hydrogen phthalate was weighed, added to 11.3 mL of 0.2 mol/L sodium hydroxide solution and an appropriate amount of water for dissolution, diluted by adding water to 100 mL, mixed homogeneously to obtain the subject solution.

3) pH 6.0 phosphate buffer solution 0.68 g of potassium dihydric phosphate was weighed, added to 2.8 mL of 0.2 mol/L sodium hydroxide solution and an appropriate amount of water for dissolution, diluted by adding water to 100 mL, mixed homogeneously to obtain the subject solution.

4) pH 7.0 phosphate buffer solution 0.68 g of potassium dihydric phosphate was weighed, added to 14.55 mL of 0.2 mol/L sodium hydroxide solution and an appropriate amount of water for dissolution, diluted by adding water to 100 mL, mixed homogeneously to obtain the subject solution.

5) pH 8.0 sodium hydroxide/potassium chloride/boric acid solution 0.75 g of potassium chloride and 0.62 g of boric acid were weighed, added to 3.9 mL of 0.2 mol/L sodium hydroxide solution and an appropriate amount of water for dissolution, diluted by adding water to 200 mL, mixed homogeneously to obtain the subject solution.

6) pH 9.0 sodium hydroxide/potassium chloride/boric acid solution 0.75 g of potassium chloride and 0.62 g of boric acid were weighed, added to 20.8 mL of 0.2 mol/L sodium hydroxide solution and an appropriate amount of water for dissolution, diluted by adding water to 200 mL, mixed homogeneously to obtain the subject solution.

6. Experimental Results:

TABLE 8

Solubility of Compound Q in buffer solutions with different pH values

| Sample | Sample size (mg) | Theoretical concentration (mg/mL) | Buffer solution (pH) | Measured concentration (mg/mL) |
|---|---|---|---|---|
| Compound Q | 1 | 1 | 3 | 0.371 |
| | | | 5 | 0.000276 |
| | | | 7 | 0.000124 |
| | | | 9 | 0.000128 |

Table 8 showed that Compound Q had very low solubility in pH 5, pH 7 and pH 9 buffer solutions, but had an increased solubility in pH 3 buffer saline aqueous solution. The reason for the increase of solubility was that Compound Q formed amine salt under acidic condition, which caused an increased solubility.

TABLE 9

Solubility values of Compound 1 of the present invention in buffer solutions with different pH values

| Buffer solution (pH value) | Sample size (mg) | Amount of buffer solution (µL) | Operation | Phenomenon | Solubility (mg/mL) |
|---|---|---|---|---|---|
| 4 | 2 | 40 | shaking | dissolved, sample was precipitated after about 5 min | / |
| | | 120 | shaking | dissolved, sample was precipitated and gradually became paste form | |
| | | 360 | shaking | not dissolved, still presented in paste form | |
| 5 | 2 | 40 | shaking | dissolved | ≥50 |
| 6 | 2 | 40 | shaking | dissolved | ≥50 |
| 7 | 2 | 40 | shaking | dissolved | ≥50 |
| 8 | 2 | 40 | shaking | dissolved | ≥50 |
| 9 | 2 | 40 | shaking | dissolved | ≥50 |

Compound 1 was completely dissolved after added to 40 µL of pH 5, pH 6, pH 7, pH 8, pH 9 buffer solutions. However, Compound 1 was dissolved at first when it was added to 40 µL of pH 4 buffer solution, and Compound 1 was precipitated after about 5 min. Compound was dissolved again after 80 µL of pH 4 buffer solution was further added, and Compound 1 was precipitated again after about 5 seconds and gradually become paste form. When 200 µL of pH 4 buffer solution was further added, Compound 1 was no longer dissolved and still presented in paste form.

Hence, the solubility of Compound 1 was greater than or equal to 50 mg/mL in pH 5, pH 6, pH 7, pH 8, pH 9 buffer solutions, but decreased in pH 4 buffer solution. The reason for the decrease of solubility was that Compound 1 changed from disodium salt of phosphate ester into phosphate monoester, so the solubility decreased when salt became ester.

7. Experimental Conclusions:

Table 8 and Table 9 showed that when pH values of buffer solutions were 5, 7, 9, the measured concentrations of Compound Q were lower than the measured concentrations of Compound 1 of the present invention in corresponding buffer solutions with same pH values.

It indicated that the solubility of Compound 1 of the present invention was significantly better than the solubility of Compound Q. The solubility of Compound 1 of the present invention increased when buffer solution gradually changed from weak acidic condition to weak alkaline condition. It is then determined that Compound 1 of the present invention would facilitate manufacture of any pharmaceutically acceptable dosage forms, especially manufacture of injections.

Experiment 5

Solubility Comparison of Compounds of the Present Invention in Water

Test Sample:

some of compounds of the present invention, prepared according to the methods in Examples.

Experimental Method:

Method for preparing samples of Compounds 4, 4-A, Compounds 9, and 9-B: 2 mg of test sample was taken, gradually added to ultrapure water, treated with ultrasound for 5 min each time until the sample was completely dissolved by visional observation.

Experimental Results:

TABLE 10

Solubility of Compounds 4, 4-A, 9, 9-B of the present invention in ultrapure water

| Sample | Sample size (mg) | Volume (mL) | Operation | Phenomenon | Result |
|---|---|---|---|---|---|
| 4 | 5 | 0.025 | ultrasound 5 min | solution clear | ≥200 mg/mL |
| 4-A | 2 | 0.04 | ultrasound 5 min | solution turbid | |
| | | 0.08 | ultrasound 5 min | solution turbid | |
| | | 0.2 | ultrasound 5 min | solution turbid | |
| | | 0.4 | ultrasound 5 min | solution turbid | |
| | | 1 | ultrasound 5 min | solution turbid | <0.1 mg/mL |
| | | 2 | ultrasound 5 min | solution turbid | |
| | | 4 | ultrasound 5 min | solution turbid | |
| | | 10 | ultrasound 5 min | solution turbid | |
| | | 20 | ultrasound 5 min | solution turbid | |

Experimental Conclusions:

The above results showed that the solubility of Compound 4 in water was 2000 times higher than the solubility of its original drug Compound 4-A in water. It can be then determined that the physical and chemical properties of the prodrug compounds of the present invention were good, which would facilitate manufacture of pharmaceutically acceptable dosage forms, especially injections, so that the development of dosage forms for clinical use would be effectively expanded.

Conclusions

The experimental results of Example 4 and Example 5 showed that the compounds of Formula (I) of the present invention had better solubility and were easy to be absorbed by animal body or human body. In addition, these experiments confirmed that they could be advantageously converted in blood into original drug compounds with good inhibition activity on PDE-5 enzyme. Thus, the compounds of the present invention would preferably exert pharmacological activity of inhibiting PDE-5 enzyme.

4. SPECIFIC EMBODIMENTS FOR THE INVENTION

The above contents of the present invention are further illustrated in detail in form of specific examples. However, it should not be interpreted that the present invention is limited to the following examples. All technologies based on the above contents of the present invention fall within the scope of the present invention.

Example 1

Preparation of N-trans-4-(2-(3-azabicyclo[3.1.0] hexan-3-yl)-4-(3-chloro-4-methoxybenzylamino) pyrimidine-5-carboxamido)cyclohexyl phosphate disodium salt (Compound 1)

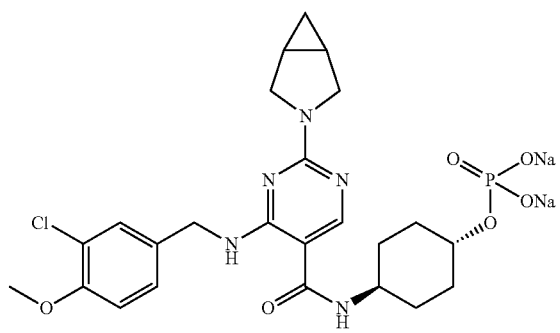

(1) Preparation of 3-benzyl-3-azabicyclo[3.1.0]hexane-2,4-dione

To a three-mouth flask, 1 L of glacial acetic acid was added, 3-oxobicyclo[3.1.0]hexane-2,4-dione (200 g, 1.784 mol) was added under stirring, and benzylamine (288 g, 2.7 mol) was added dropwise under ice-water bath. After dropwise addition, the reaction was slowly warmed and refluxed at 130° C. and stirred for 12 h, TLC was used to monitor the reaction. After the end of reaction, reaction liquid was cooled to room temperature, poured into water (10 L) to precipitate a large amount of white solid. After filtration, the filter cake was washed with isopropanol in amount of 0.8 times mass, filtrated and vacuum dried to obtain 270 g of white solid product, the yield was 75%.

(2) Preparation of 3-benzyl-3-azabicyclo[3.1.0]hexane hydrochloride

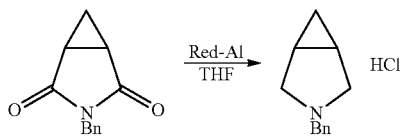 [SMILES: O=C1C2CC2C(=O)N1Cc1ccccc1 ; "Red-Al" ; c1ccc(CN2CC3CC3C2)cc1 ; Cl ; "THF"]

To a three-mouth flask, 1.5 L of tetrahydrofuran was added, Red-Al (70% toluene solution) (1148 mL, 3.976 mol) was added under stirring, then 3-benzyl-3-azabicyclo[3.1.0] hexane-2,4-dione (200 g, 0.994 mol) in THF (50 mL) was added dropwise. The reaction was stirred at room temperature for 12 h. TLC was used to monitor reaction. After the end of reaction, the reaction was quenched by carefully adding water (200 mL) dropwise under ice-water bath. Ethyl acetate (500 mL) was added, filtration was carried out by using diatomite, and tetrahydrofuran was distilled off under reduced pressure. Ethyl acetate (1 L) was added, liquid phases were separated, the water phase was extracted with ethyl acetate (300 mL), the organic phases were combined and washed with saturated sodium chloride aqueous solution (300 mL), dried over anhydrous sodium sulfate, filtrated, evaporated to remove solvent. MTBE (500 mL) was added, hydrogen chloride-ethanol solution (100 mL) was added dropwise at about −20° C., and pH value was regulated to 1-2. As a large amount of white solid was precipitated, MTBE (500 mL) was added again, the mixture was stirred for 30 min at low temperature, and white solid (180 g, yield of 86.3%) was obtained after suction filtration and air-drying.

(3) Preparation of 3-azabicyclo[3.1.0]hexane hydrochloride

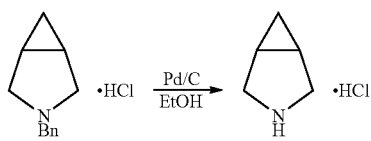 [SMILES: "EtOH" ; c1ccc(CN2CC3CC3C2)cc1 ; Cl ; "Pd/C" ; C1NCC2CC12 ; Cl]

To a three-mouth flask, 3-benzyl-3-azabicyclo[3.1.0] hexane hydrochloride (120 g, 572 mmol) was dissolved in ethanol (1000 mL), 10% Pd/C (17 g) was added, the reaction was stirred overnight under hydrogen gas atmosphere at room temperature. LC-MS was used to monitor the reaction. After the end of reaction, filtration was carried out by using diatomite, the filter liquor was directly concentrated by rotary evaporation, washed with a small amount of ethyl acetate and dried to give white solid product (61.6 g, yield of 91.3%).

(4) Preparation of ethyl 4-(3-chloro-4-methoxy-benzylamino)-2-methylthiopyrimidine-5-carboxylate

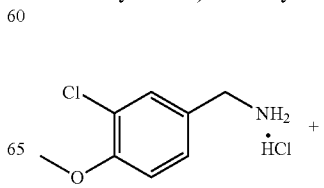

-continued

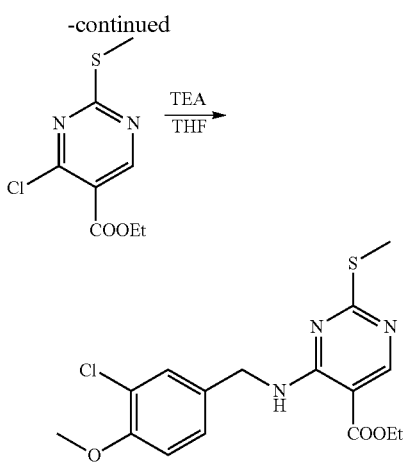

In a flask, tetrahydrofuran (4.5 L) was added, 3-chloro-4-methoxybenzylamine hydrochloride (500 g, 2.4 mol) was added under stirring, triethylamine (836 mL, 6.01 mol) was added dropwise, the mixture was stirred at room temperature for 30 min, cooled with ice-water, then ethyl 4-chloro-2-methylthiopyrimidine-5-carboxylate(466 g, 2.0 mol) was added, the reaction was stirred overnight at room temperature. TLC was used to monitor the reaction. After the end of reaction, solvent was removed by evaporation under reduced pressure. Ethyl acetate (2.5 L) and water (1 L) were added, the mixed liquid phases were separated, the organic phase was sequentially washed with diluted hydrochloric acid, water (1 L), saturated sodium bicarbonate (1 L) and saturated sodium chloride (1 L), dried over anhydrous sodium sulfate. After filtration, solvent was removed by evaporation under reduced pressure to obtain an oily substance, to which was added methanol (3 L), and a large white solid was precipitated. After stirring for 30 min, filtration was carried out, and the filter cake was vacuum dried to obtain the product (650 g, yield of 88.3%).

(5) Preparation of ethyl 4-(3-chloro-4-methoxy-benzylamino)-2-methylsulfinylpyrimidine-5-carboxylate

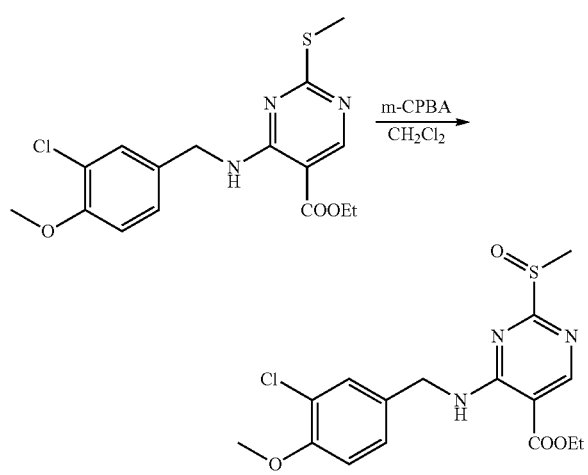

To a reaction flask, dichloromethane (3 L) was added, ethyl 4-(3-chloro-4-methoxybenzylamino)-2-methylthiopyrimidine-5-carboxylate (500 g, 1.359 mol) was added under stirring, then m-chloroperoxybenzoic acid (235 g, 1.359 mol) in dichloromethane (1 L) solution was added dropwise under ice-water bath. After the end of dropwise addition, the temperature of the reaction was naturally elevated to room temperature. TLC was used to monitor the reaction. After stirring for 2 h, raw materials did not react completely, m-chloroperoxybenzoic acid (70 g, 0.4 mol) was added, and the reaction was continuously stirred for 2 h. After the end of reaction, saturated sodium bicarbonate solution (1 L) was used to quench the reaction. The organic phase was separated, and the water phase was extracted with dichloromethane. The organic phases were combined, washed sequentially with saturated sodium bicarbonate, saturated sodium chloride aqueous solution, and dried over anhydrous sodium sulfate, filtrated, and directly used in next reaction without further purification.

(6) Preparation of ethyl 2-(3-azabicyclo[3.1.0]hexan-3-yl)-4-(3-chloro-4-methoxybenzylamino)-pyrimidine-5-carboxylate

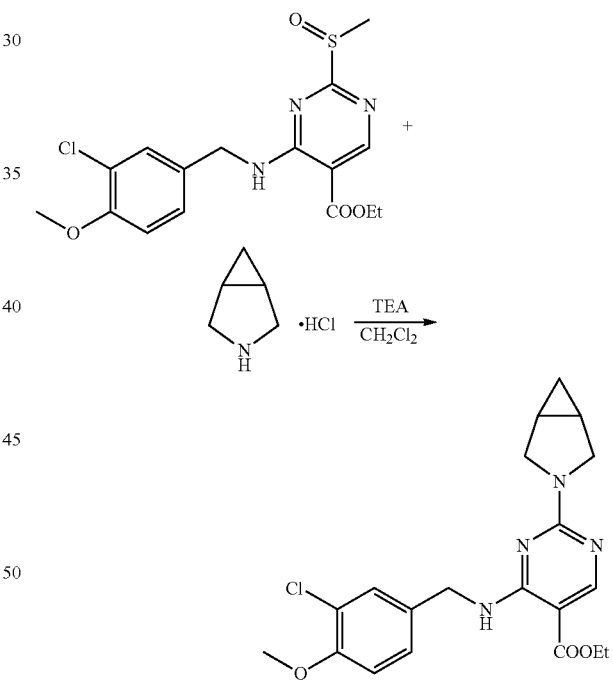

To a reaction flask, the dried filter liquor of ethyl 4-(3-chloro-4-methoxy-benzylamino)-2-methylsulfinylpyrimidine-5-carboxylate was added, 3-azabicyclo[3.1.0]hexane hydrochloride (178.8 g, 1.5 mol) was added under stirring, triethylamine (284 mL, 2.04 mol) was added dropwise under ice-bath. After the end of dropwise addition, the temperature reaction was naturally elevated to room temperature. TLC was used to monitor reaction. After stirring overnight at room temperature, the reaction was quenched by addition of saturated ammonium chloride (1 L). The organic phase was separated, and the water phase was extracted with dichloromethane. The organic phases were combined, sequentially washed with diluted hydrochloric acid, saturated sodium bicarbonate, and saturated sodium chloride, dried over anhydrous sodium sulfate and filtrated, an oily substance was obtained after solvent was removed by evaporation under reduced pressure. 3 L of methanol was added to precipitate a large amount of white solid, stirred for 30 min, vacuum filtered to obtain a white solid of ethyl 2-(3-azabicyclo[3.1.0]hexan-3-yl)-4-(3-chloro-4-methoxy benzylamino)pyrimidine-5-carboxylate (485 g, yield of 88.6%).

(7) Preparation of 2-(3-azabicyclo[3.1.0]hexan-3-yl)-4-(3-chloro-4-methoxybenzylamino)-pyrimidine-5-carboxylic acid (8) Preparation of 2-(3-azabicyclo[3.1.0]hexan-3-yl)-4-(3-chloro-4-methoxybenzylamino)-N-(trans-4-hydroxycyclohexyl)pyrimidine-5-carboxamide (Compound Q)

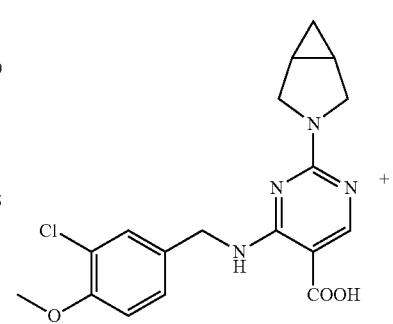

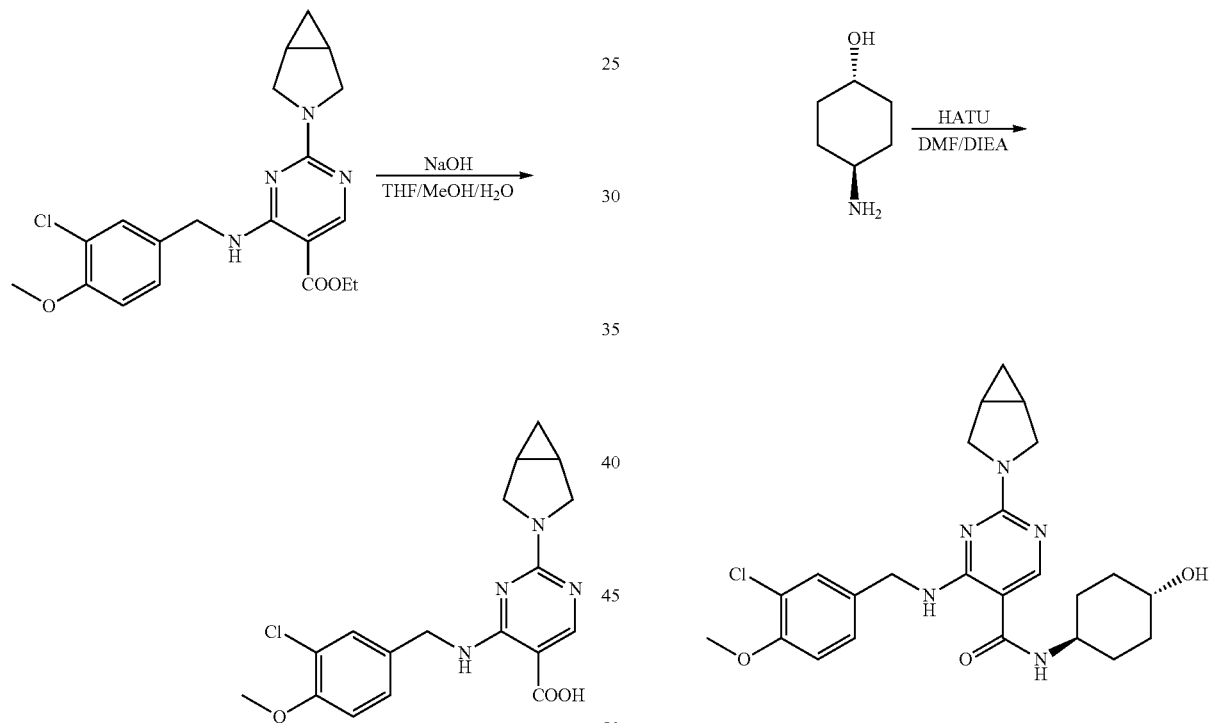

To a reaction flask, tetrahydrofuran (40 mL) and methanol (20 mL) were added, ethyl 2-(3-azabicyclo[3.1.0]hexan-3-yl)-4-(3-chloro-4-methoxybenzylamino)pyrimidine-5-carboxylate (485 g, 1.2 mol) was added under stirring, then 3N sodium hydroxide solution (1.2 L, 3.6 mmol) was added dropwise, and the reaction was heated until refluxed. TLC was used to monitor the reaction. After stirring overnight, the reaction was completed and cooled to room temperature, 3N HCl (200 mL, 0.8 mol) was added to regulate pH=3 to precipitate white solid. Tetrahydrofuran and methanol were removed by evaporation under reduced pressure, water (500 mL) was added, stirred for 1 h, filtered and vacuum dried to obtain 2-(3-azabicyclo[3.1.0]hexan-3-yl)-4-(3-chloro-4-methoxybenzylamino)pyrimidine-5-carboxylic acid (450 g, yield of 99.6%).

To a reaction flask, DMF (2 L) was added, 2-(3-azabicyclo[3.1.0]hexan-3-yl)-4-(3-chloro-4-methoxybenzylamino) pyrimidine-5-carboxylic acid (300 g, 0.8 mol) was added under stirring, DIEA (209 mL, 1.2 mol) was added dropwise under ice-water, then HATU (456 g, 1.2 mol) was added, the mixture was stirred for 30 min, trans-4-aminocyclohexanol (138.2 g, 1.2 mol) was added. The temperature of the reaction was naturally elevated to room temperature, stirring was carried out for 2 h, and TLC was used to monitor the reaction. After the end of reaction, the reaction liquid was poured into water (3 L) to precipitate solid and filtrated, the filter cake was washed with water, air-dried, then recrystallized with acetone twice to obtain white solid (240 g, yield of 63%).

(9) Preparation of N-trans-4-(2-(3-azabicyclo[3.1.0]hexan-3-yl)-4-(3-chloro-4-methoxy benzylamino)pyrimidine-5-carboxamido)cyclohexyl dihydrogen phosphate

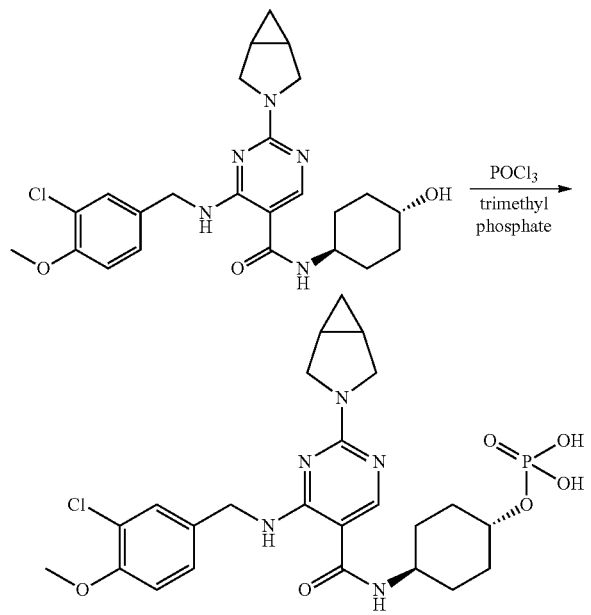

2-(3-azabicyclo[3.1.0]hexan-3-yl)-4-(3-chloro-4-methoxybenzylamino)-N-(trans-4-hydroxy cyclohexyl)pyrimidine-5-carboxamide (1.0 g, 2.1 mmol) was dissolved in trimethyl phosphate (14 mL), POCl₃ (1.62 g, 10.6 mmol) was added dropwise under ice bath condition. The reaction liquid was stirred at room temperature for 12 h, LC-MS was used to monitor the reaction until the end of reaction. The reaction liquid was cooled in ice-water bath, NaHCO₃ (2.35 g, 27.97 mmol) aqueous solution was added dropwise, a large amount of white solid was generated. After filtration, the white solid was purified by preparative chromatograph (C₁₈ column, H₂O/CH₃CN:100:0-80:20) to obtain N-trans-4-(2-(3-azabicyclo[3.1.0]hexan-3-yl)-4-(3-chloro-4-methoxybenzylamino)-pyrimidine-5-carboxamido)cyclohexyl dihydrogen phosphate (0.5 g, yield of 43.1%).

(10) Preparation of N-trans-4-(2-(3-azabicyclo[3.1.0]hexan-3-yl)-4-(3-chloro-4-methoxy benzylamino)pyrimidine-5-carboxamido)cyclohexyl phosphate disodium salt

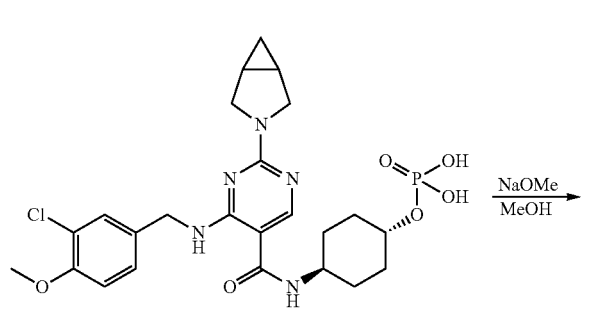

-continued

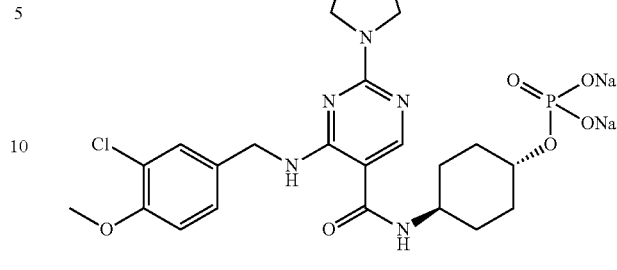

N-trans-4-(2-(3-azabicyclo[3.1.0]hexan-3-yl)-4-(3-chloro-4-methoxybenzylamino)pyrimidine-5-carboxamido)cyclohexyl dihydrogen phosphate (500 mg, 0.91 mmol) was suspended in anhydrous methanol (10 mL), sodium methoxide (9.8 mg, 1.82 mmol) was added under ice-water bath, the solution became clear, stirring was carried out for 3 h, a small amount of insoluble substance appeared. The solution was filtered, the filter liquor was evaporated to dryness under reduced pressure, the obtained solid was washed with water and acetone in small amounts to obtain white solid of N-trans-4-(2-(3-azabicyclo[3.1.0]hexan-3-yl)-4-(3-chloro-4-methoxybenzylamino)pyrimidinde-5-carboxamido)cyclohexyl phosphate disodium salt (350 mg, yield of 64.5%).

Molecular Formula: $C_{24}H_{29}ClN_5Na_2O_6P$ Molecular weight: 595.9 MS (m/z): 551.9 (M+1)

$^1$H-NMR (400 MHz, CD₃OD-d₄) δ: 8.21 (s, 1H), 7.37 (s, 1H), 7.23-7.26 (m, 1H), 7.01 (d, J=8.4 Hz, 1H), 4.55 (s, 2H), 4.01-4.03 (m, 1H), 3.85 (s, 3H), 3.72-3.80 (m, 3H), 3.45-3.48 (m, 2H), 2.26-2.28 (m, 2H), 1.85-1.95 (m, 2H), 1.62-1.64 (m, 2H), 1.39-1.48 (m, 4H), 0.73-0.78 (m, 1H), 0.11-0.14 (m, 1H).

Example 2

Preparation of N-trans-4-(4-((3-chloro-4-methoxybenzyl)amino)-2-(5-azaspiro[2.4]heptan-5-yl)pyrimidine-5-carboxamido)cyclohexyl phosphate disodium salt (Compound 4)

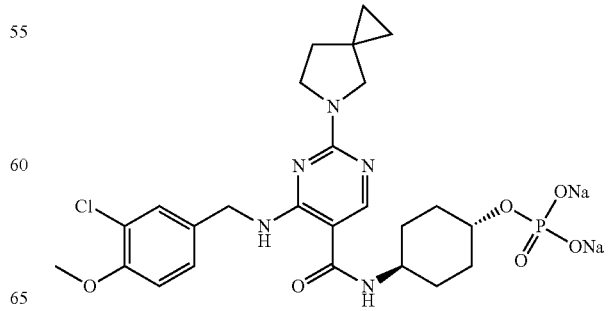

(1) Preparation of ethyl 4-(3-chloro-4-methoxybenzylamino)-2-(methylsulfinyl)pyrimidine-5-carboxylate

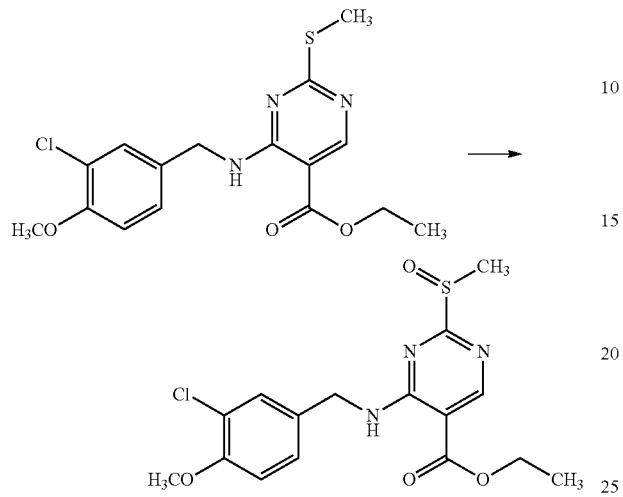

Ethyl 4-(3-chloro-4-methoxybenzylamino)-2-(methylthio)pyrimidine-5-carboxylate (200 mg, 0.59 mmol) was dissolved in dichloromethane (20 mL), m-CPBA (101 mg, 0.59 mmol) was added under ice-water bath, the reaction was heated to room temperature and conducted for 5 h. Water was added to the reaction and extracted with dichloromethane. The organic layer was dried, concentrated to obtain solid. The product was used in next reaction without any purification.

(2) Preparation of ethyl 4-(3-chloro-4-methoxybenzylamino)-2-(5-azaspiro[2.4]heptan-5-yl)-pyrimidine-5-carboxylate

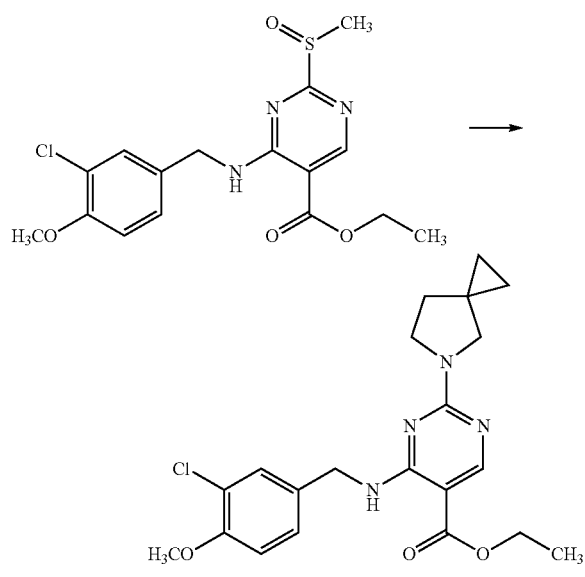

Ethyl 4-(3-chloro-4-methoxybenzylamino)-2-(methylsulfinyl)pyrimidine-5-carboxylate (196 mg, 0.55 mmol) and 5-azaspiro[2.4]heptane hydrochloride (14.6 mg, 0.109 mmol) were dissolved in tetrahydrofuran (15 mL), triethylamine (167 mg, 1.65 mmol) was added dropwise under ice-water bath, the reaction was heated to room temperature and conducted for 5 h. Water was added to the reaction and extracted with dichloromethane. The organic layer was dried, concentrated to obtain solid. The product was used in next reaction without any purification.

(3) Preparation of 4-(3-chloro-4-methoxybenzylamino)-2-(5-azaspiro[2.4]heptan-5-yl)-pyrimidine-5-carboxylic acid

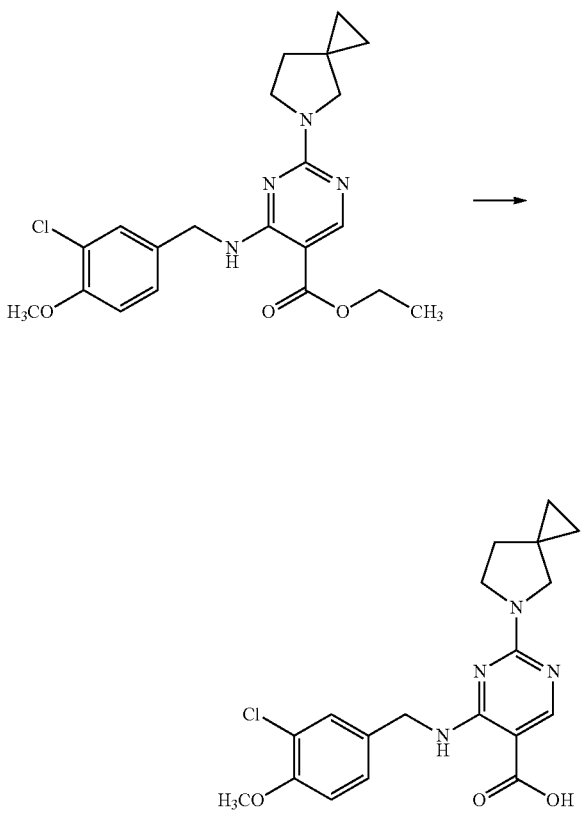

Ethyl 4-((3-chloro-4-methoxybenzyl)amino)-2-(5-azaspiro[2.4]heptan-5-yl)pyrimidine-5-carboxylate (3.4 g, 8.17 mmol) and sodium hydroxide (1.14 g, 28.57 mmol) were dissolved in the mixture of water (10 mL), methanol (30 mL) and tetrahydrofuran (30 mL), the reaction was conducted at 60° C. for 10 h. The reaction liquid was cooled to room temperature and diluted with hydrochloric to regulate pH=4. Solid was precipitated, filtrated, washed with methanol, and dried to obtain 4-(3-chloro-4-methoxybenzylamino)-2-(5-azaspiro[2.4]heptan-5-yl)-pyrimidine-5-carboxylic acid (1.7 g, yield of 54%).

(4) Preparation of ethyl 4-(3-chloro-4-methoxyben-zylamino)-N-(trans-4-hydroxycyclohexyl)-2-(5-azaspiro[2.4]heptan-5-yl)pyrimidine-5-carboxamide (Compound 4-A)

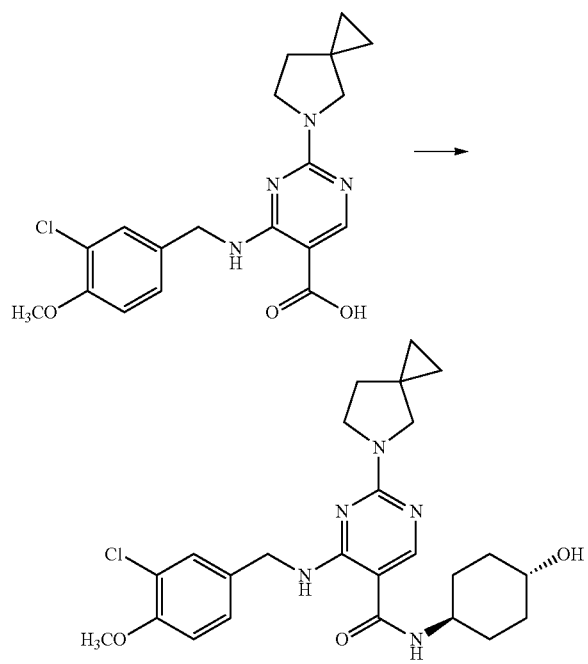

4-(3-chloro-4-methoxybenzylamino)-2-(5-azaspiro[2.4]heptan-5-yl)pyrimidine-5-carboxylic acid (210 mg, 0.54 mmol), trans-4-aminocyclohexanol (138.2 g, 1.2 mol) and triethylamine (0.2 mL) were dissolved in THF (50 mL), HATU (266 mg, 0.70 mmol) was added under ice-water bath. Reaction was carried out at room temperature for 18 h, water was added after concentration, extracted with ethyl acetate. The organic layer was dried and concentrated, and then separated via silica gel column (dichloromethane:methanol=50:1) to obtain the title compound (115 mg, yield of 44%).

(5) Preparation of N-trans-4-(4-((3-chloro-4-methoxybenzyl)amino)-2-(5-azaspiro[2.4]heptan-5-yl)pyrimidine-5-carboxamido)cyclohexyl dihydrogen phosphate

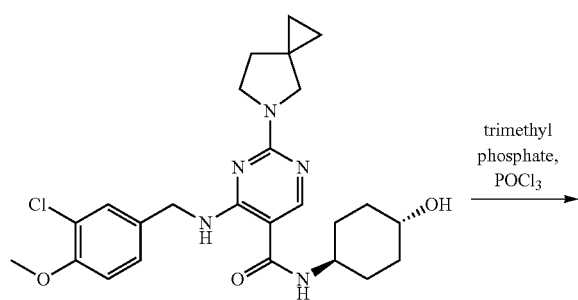

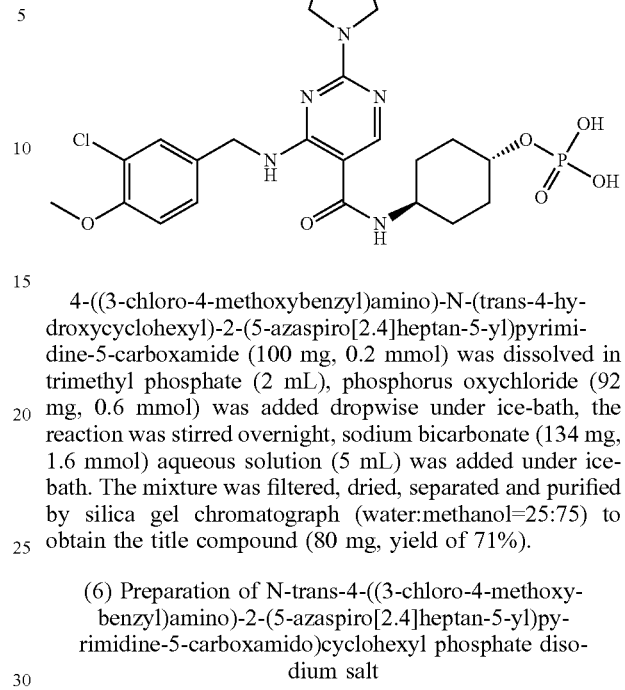

4-((3-chloro-4-methoxybenzyl)amino)-N-(trans-4-hydroxycyclohexyl)-2-(5-azaspiro[2.4]heptan-5-yl)pyrimidine-5-carboxamide (100 mg, 0.2 mmol) was dissolved in trimethyl phosphate (2 mL), phosphorus oxychloride (92 mg, 0.6 mmol) was added dropwise under ice-bath, the reaction was stirred overnight, sodium bicarbonate (134 mg, 1.6 mmol) aqueous solution (5 mL) was added under ice-bath. The mixture was filtered, dried, separated and purified by silica gel chromatograph (water:methanol=25:75) to obtain the title compound (80 mg, yield of 71%).

(6) Preparation of N-trans-4-((3-chloro-4-methoxybenzyl)amino)-2-(5-azaspiro[2.4]heptan-5-yl)pyrimidine-5-carboxamido)cyclohexyl phosphate disodium salt N-trans-4-(4-((3-chloro-4-methoxybenzyl)amino)-2-(5-azaspiro[2.4]heptan-5-yl)pyrimidin-5-carboxamido)cyclohexyl dihydrogen phosphate (80 mg, 0.14 mmol) was dissolved in methanol (2 mL), sodium methoxide (15 mg, 0.28 mmol) was added. The reaction was stirred at room temperature for 2 h and dried by rotary evaporation to obtain the title compound (60 mg, yield of 70%).

Molecular Formula: $C_{25}H_{31}ClN_5Na_2O_6P$; Molecular Weight: 610.0; LC-MS (m/z): 611 (M+1)

$^1$H-NMR (400 MHz, $CD_3OD$-$d_4$) δ: 8.55 (s, 1H), 8.27 (s, 1H), 7.36 (s, 1H), 7.24 (d, J=8.4 Hz, 1H), 7.00 (d, J=8.4 Hz,

1H), 4.54 (s, 2H), 4.03-4.04 (m, 1H), 3.85 (s, 3H), 3.67-3.79 (m, 3H), 3.40 (s, 2H), 2.27 (s, 2H), 1.87-1.90 (m, 4H), 1.40-1.49 (m, 4H), 0.63-0.64 (m, 4H).

Example 3

Preparation of N-trans-4-(2-(3-azabicyclo[3.1.0]hexan-3-yl)-4-((4-methoxy-3-methylbenzyl)amino)pyrimidine-5-carboxamido)cyclohexyl phosphate disodium salt (Compound 9)

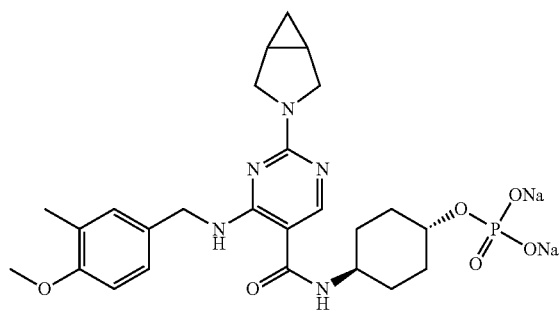

(1) Preparation of ethyl 4-(4-methoxy-3-methylbenzylamino)-2-(methylthio)pyrimidine-5-carboxylate

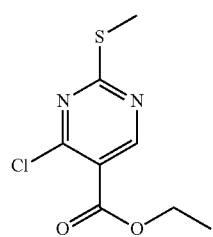

Ethyl 4-chloro-2-(methylthio)pyrimidine-5-carboxylate (1.5 g, 6.46 mmol), 3-methyl-4-methoxy benzylamine (0.72 g, 4.7 mmol) and triethylamine (1.3 g, 12.9 mmol) were dissolved in dichloromethane (50 mL), the reaction was stirred at room temperature for 30 min. The reaction liquid was washed with water, the organic layer was dried over anhydrous sodium sulfate, concentrated to obtain the title compound (2.1 g, yield of 92%) in yellow oil.

(2) Preparation of ethyl 4-(4-methoxy-3-methylbenzylamino)-2-(methylsulfinyl)pyrimidine-5-carboxylate

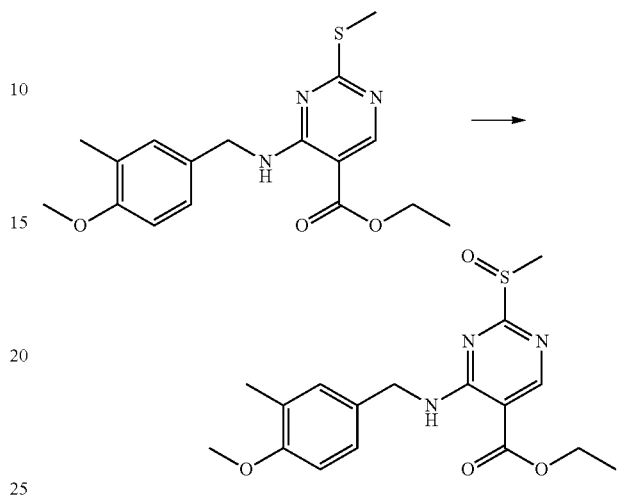

Ethyl 4-(4-methoxy-3-methylbenzylamino)-2-(methylthio)pyrimidine-5-carboxylate ester (2.2 g, 6.3 mmol) was dissolved in dichloromethane (50 mL), m-CPBA (m-chloroperoxybenzoic acid, 1.1 g, 6.4 mmol) was added, the reaction was conducted at room temperature for 30 min. The reaction liquid was then washed with water, the organic layer was dried over anhydrous sodium sulfate, concentrated to obtain the title compound, and the product was used in next reaction without any purification.

(3) Preparation of ethyl 2-(3-azabicyclo[3.1.0]hexan-3-yl)-4-(4-methoxy-3-methylbenzyl amino)pyrimidine-5-carboxylate

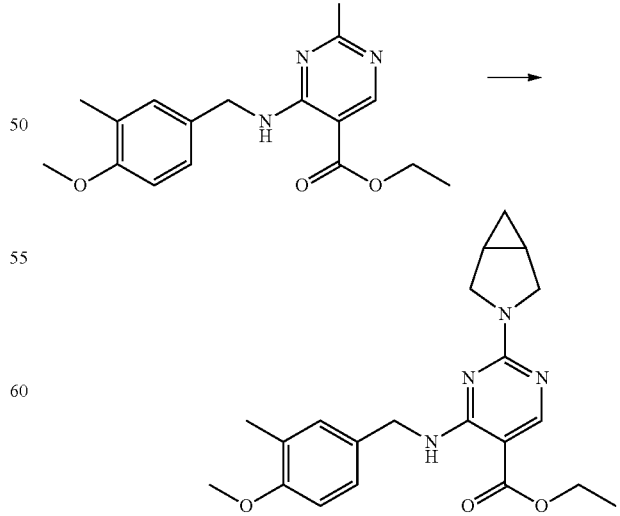

The above product ethyl 4-(4-methoxy-3-methylbenzylamino)-2-(methylsulfinyl)pyrimidine-5-carboxylate was dissolved in dichloromethane (50 mL), 3-azabicyclo[3.1.0]hexane hydrochloride (0.8 g, 6.67 mmol) and triethylamine (4 mL, 28.8 mmol) were added. The reaction was carried out at room temperature for 18 h, water was added to the reaction liquid and extracted with dichloromethane. The organic phase was dired over anhydrous sodium sulfate and by rotary evaporation to obtain 3.1 g of the title compound in faint yellow oil, and this product was used in next reaction without any purification.

(4) Preparation of 2-(3-azabicyclo[3.1.0]hexan-3-yl)-4-(4-methoxy-3-methylbenzylamino)-pyrimidine-5-carboxylic acid

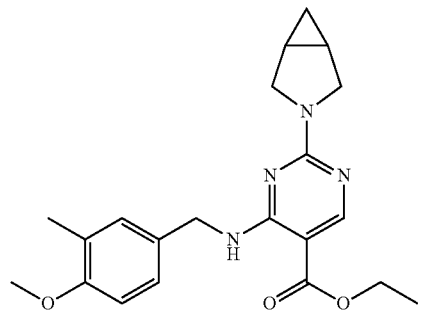

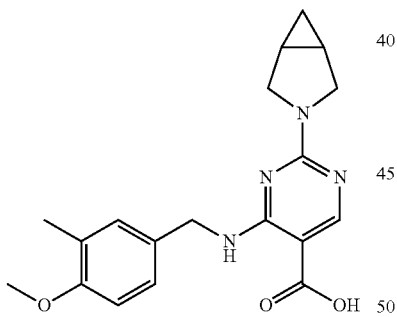

Ethyl 2-(3-azabicyclo[3.1.0]hexan-3-yl)-4-(4-methoxy-3-methylbenzylamino)pyrimidine-5-carboxylate (1.5 g, 3.9 mmol) and sodium hydroxide (260 mg, 6.5 mmol) were dissolved in the mixture of water (5 mL), ethanol (5 mL) and THF (15 mL), the reaction was carried out at room temperature for 5 h. After solvents were distilled off, water was added and washed with dichloromethane, the water phase was regulated with diluted hydrochloride acid to pH=2, extracted with dichloromethane again. The organic phase was dried over anhydrous sodium sulfate and concentrated to obtain the title compound (1.2 g, yield of 86%) in faint yellow solid.

(5) Preparation of 2-(3-azabicyclo[3.1.0]hexan-3-yl)-N-(trans-4-hydroxycyclohexyl)-4-(4-methoxy-3-methylbenzylamino)pyrimidine-5-carboxamide (Compound 9-B)

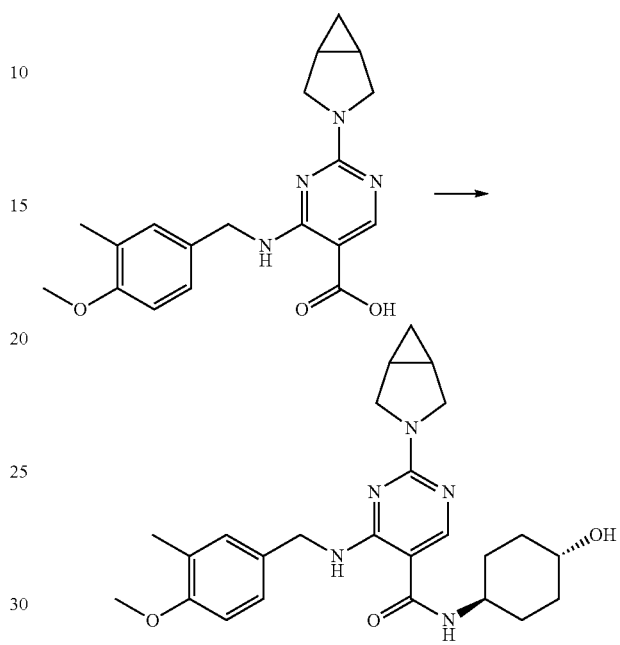

2-(3-azabicyclo[3.1.0]hexan-3-yl)-4-(4-methoxy-3-methylbenzylamino)pyrimidine-5-carboxylic acid (574 mg, 1.62 mmol), trans-4-hydroxycyclohexylamine (187 mg, 1.62 mmol), TEA (485 mg, 4.79 mmol) and HATU (2-(7-azobenzotriazolyl)-N,N,N',N'-tetramethyluronium hexafluorophosphate, 743 mg, 1.95 mmol) were dissolved in dichloromethane (20 mL) and tetrahydrofuran (20 mL), the reaction was conducted at room temperature for 17 h. Solvents were distilled off, water was added and then extracted with dichloromethane. The organic phase was dried over anhydrous sodium sulfate, concentrated and separated by silica gel column (dichloromethane:methanol=50:1) to obtain the title compound (380 mg, 52%) in faint yellow solid.

(6) Preparation of N-trans-4-(2-(3-azabicyclo[3.1.0]hexan-3-yl)-4-((4-methoxy-3-methyl-benzyl)amino)pyrimidine-5-carboxamido)cyclohexyl dihydrogen phosphate

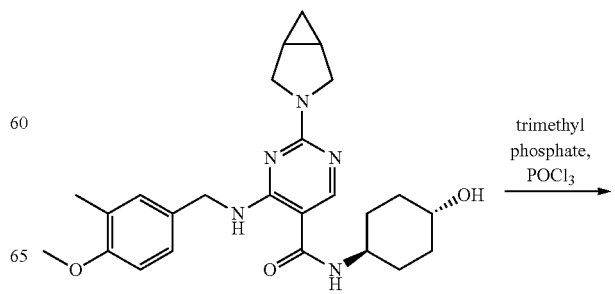

-continued

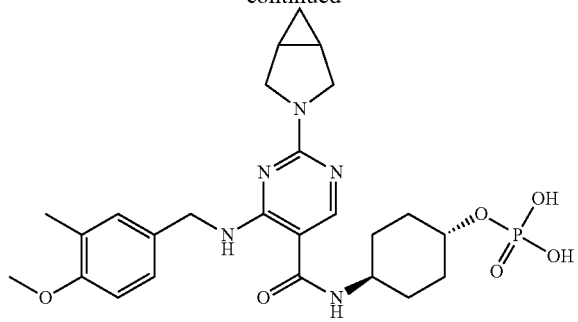

2-(3-azabicyclo[3.1.0]hexan-3-yl)-N-(trans-4-hydroxy-cyclohexyl)-4-((4-methoxy-3-methyl-benzyl)amino)pyrimidine-5-carboxamide (100 mg, 0.22 mmol) was dissolved in trimethyl phosphate (2 mL), phosphorus oxychloride (101 mg, 0.66 mmol) was added dropwise under ice-bath, the reaction was stirred overnight. Sodium bicarbonate (148 mg, 1.76 mmol) aqueous solution (5 mL) was added dropwise under ice-bath. The mixture was filtered, dried, separated and purified by silica gel chromatograph (water:methanol=30:70) to obtain the title compound (30 mg, yield of 26%).

(7) Preparation of N-trans-4-(2-(3-azabicyclo[3.1.0]hexan-3-yl)-4-((4-methoxy-3-methylbenzyl)amino)pyrimidin-5-carboxamido)cyclohexyl phosphate disodium salt

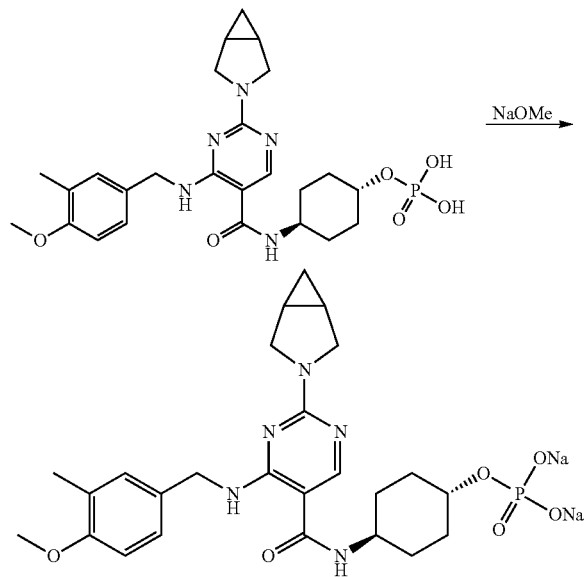

N-trans-4-(2-(3-azabicyclo[3.1.0]hexan-3-yl)-4-((4-methoxy-3-methylbenzyl)amino)pyrimidine-5-carboxamido)cyclohexyl dihydrogen phosphate (30 mg, 0.056 mmol) was dissolved in methanol (1 mL), sodium methoxide (6 mg, 0.112 mmol) was added, the reaction was stirred at room temperature for 2 h, dried by rotary evaporation to obtain the title compound (28 mg, yield of 87.5%).

Molecular Formula: $C_{25}H_{32}N_5Na_2O_6P$; Molecular Weight: 575.5; LC-MS (m/z): 576 (M+1)

$^1$H-NMR (400 MHz, $CD_3OD$-$d_4$) δ: 8.55 (s, 1H), 8.24 (s, 1H), 7.12-7.14 (m, 2H), 6.83 (d, J=8 Hz, 1H), 4.52 (s, 2H), 4.02-4.03 (m, 1H), 3.81-3.85 (m, 1H), 3.80 (s, 3H), 3.73-3.76 (m, 2H), 3.47-3.50 (m, 2H), 2.26 (s, 2H), 2.17 (s, 3H), 1.88-1.89 (m, 2H), 1.63-1.65 (m, 2H), 1.39-1.44 (m, 4H), 0.76-0.78 (m, 1H), 0.14-0.15 (m, 1H).

What is claimed is:

1. A compound of Formula (I), pharmaceutically acceptable salts or stereoisomers thereof:

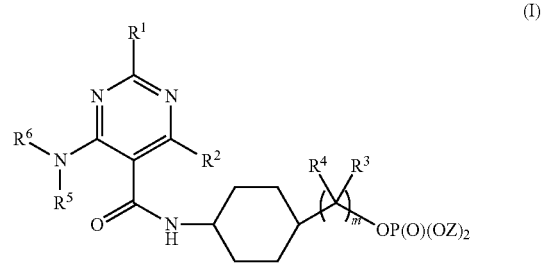

wherein $R^1$ represents 6- or 7-membered nitrogen-containing fused heterocyclyl, 7- to 12-membered nitrogen-containing spiral heterocyclyl, or 7- to 12-membered nitrogen-containing bridged heterocyclyl, any of which is optionally substituted with 1-4 substituent groups, and $R^1$ links to pyrimidine ring of Formula (I) via N atom, the substituent groups are selected from halogen atoms, cyano, amino, hydroxyl, $C_{1-6}$ alkyl, halo $C_{1-6}$ alkyl, hydroxyl $C_{1-6}$ alkyl, $C_{1-6}$ alkoxy, $C_{1-6}$ alkylcarbonyl or $C_{1-6}$ alkoxycarbonyl;

$R^2$ represents hydrogen atom, hydroxyl, amino, cyano, $C_{1-6}$ alkylamino, di($C_{1-6}$ alkyl)amino, $C_{1-6}$ alkyl, halo $C_{1-6}$ alkyl, hydroxyl $C_{1-6}$ alkyl or $C_{1-6}$ alkoxy;

$R^3$ and $R^4$ each independently represent hydrogen, or $C_{1-6}$ alkyl optionally substituted with 1-3 halogen atoms, hydroxyl, carboxyl;

m is 0 to 3;

Z is hydrogen, or a cation of inorganic base or organic base capable of forming a salt with phosphoric acid;

$R^5$ and $R^6$ each independently represent hydrogen atom or -Q-$R^7$,

Q represents a bond, or optionally substituted $C_{1-6}$ alkylidene, the substituent groups are selected from halogen atoms, hydroxyl, $C_{1-6}$ alkyl, amino, cyano, nitro or $C_{1-6}$ alkoxy;

$R^7$ is selected from 6- to 14-membered aryl, 5- to 7-membered heterocyclyl or 8- to 10-membered fused cyclyl, any of which is optionally substituted with 1-4 substituent groups, the substituent groups are selected from halogen atoms, hydroxyl, $C_{1-6}$ alkyl, halo $C_{1-6}$ alkyl, carboxyl $C_{1-6}$ alkyl, $C_{2-6}$ alkenyl, $C_{2-6}$ alkynyl, $C_{1-6}$ alkoxy, halo $C_{1-6}$ alkoxy, amino, $C_{1-6}$ alkylamino, di($C_{1-6}$ alkyl)amino, cyano, nitro, $C_{1-6}$ alkylcarbonyl, sulfonylamino or $C_{1-6}$ alkylsulfonylamino.

2. The compound according to claim 1, pharmaceutically acceptable salts or stereoisomers thereof:

wherein $R^2$ is hydrogen atom, hydroxyl or methyl;

$R^6$ represents hydrogen atom.

3. The compound according to claim 2, pharmaceutically acceptable salts or stereoisomers thereof:

wherein $R^3$ and $R^4$ are independently selected from hydrogen;

m is 0, 1 or 2;

Z is hydrogen, or sodium ion.

4. The compound according to claim 3, pharmaceutically acceptable salts or stereoisomers thereof:
wherein $R^5$ represents -Q-$R^7$,
Q is selected from $C_{1-6}$ alkylidene,
$R^7$ is selected from 6- to 10-membered aryl, 5- to 7-membered heterocyclyl or 8- to 10-membered fused cyclyl, any of which is optionally substituted with 1-4 substituent groups,
the substituent groups are selected from halogen atoms, hydroxyl, $C_{1-6}$ alkyl, halo $C_{1-6}$ alkyl, carboxyl $C_{1-6}$ alkyl, $C_{1-6}$ alkoxy, halo $C_{1-6}$ alkoxy, amino, $C_{1-6}$ alkylamino, di($C_{1-6}$ alkyl)amino, cyano, nitro, $C_{1-6}$ alkylcarbonyl, sulfonylamino or $C_{1-6}$ alkylsulfonylamino.

5. The compound according to claim 4, pharmaceutically acceptable salts or stereoisomers thereof:
wherein $R^1$ represents 6- or 7-membered nitrogen-containing fused heterocyclyl, 7- to 12-membered nitrogen-containing spiral heterocyclyl, or 7- to 12-membered nitrogen-containing bridged heterocyclyl, any of which is optionally substituted with 1-4 substituent groups, and $R^1$ links to pyrimidine ring of Formula (I) via N atom,
the substituent groups are selected from halogen atoms, cyano, amino, hydroxyl, $C_{1-6}$ alkyl, halo $C_{1-6}$ alkyl, hydroxyl $C_{1-6}$ alkyl, $C_{1-6}$ alkoxy, $C_{1-6}$ alkylcarbonyl or $C_{1-6}$ alkoxycarbonyl.

6. The compound according to claim 5, pharmaceutically acceptable salts or stereoisomers thereof:
wherein $R^1$ is selected from 6- or 7-membered nitrogen-containing fused heterocyclyl, 7- to 10-membered nitrogen-containing spiral heterocyclyl, or 7- to 8-membered nitrogen-containing bridged heterocyclyl, any of which is optionally substituted with 1-3 substituent groups, and $R^1$ links to pyrimidine ring of Formula (I) via N atom,
the substituent groups are selected from halogen atoms, cyano, amino, hydroxyl, $C_{1-4}$ alkyl, halo $C_{1-4}$ alkyl, hydroxyl $C_{1-4}$ alkyl, or $C_{1-4}$ alkoxy;
$R^3$ and $R^4$ each independently are hydrogen;
m is 0, 1 or 2;
Z is hydrogen, or sodium ion;
$R^5$ represents -Q-$R^7$,
Q is selected from $C_{1-4}$ alkylidene,
$R^7$ is selected from phenyl, 5- to 7-membered heterocyclyl or 8- to 10-membered fused cyclyl, any of which is optionally substituted with 1-3 substituent groups,
the substituent groups are selected from halogen atoms, methyl, trifluoromethyl, methoxy, ethoxy, trifluoromethoxy, dimethylamino or carboxymethyl;
$R^2$ is selected from hydrogen atom;
$R^6$ is selected from hydrogen atom.

7. The compound according to claim 6, pharmaceutically acceptable salts or stereoisomers thereof:
wherein $R^1$ is selected from 6- or 7-membered nitrogen-containing fused heterocyclyl, or 7- to 10-membered nitrogen-containing spiral heterocyclyl, any of which is optionally substituted with 1-3 substituent groups, and $R^1$ links to pyrimidine ring of Formula (I) via N atom,
the substituent groups are selected from halogen atoms, cyano, amino, hydroxyl, $C_{1-4}$ alkyl, halo $C_{1-4}$ alkyl, hydroxyl $C_{1-4}$ alkyl, or $C_{1-4}$ alkoxy;
$R^3$ and $R^4$ are independently selected from hydrogen;
m is 0, 1 or 2;
Z is hydrogen, or sodium ion;
$R^5$ represents -Q-$R^7$,
Q is selected from methylene or ethylene,
$R^7$ is selected from phenyl, pyrrolyl, furyl, pyridyl, thiazolyl, naphthyl, benzopyrrolyl, indenyl, quinolyl or indolyl, any of which is optionally substituted with 1-3 substituent groups,
the substituent groups are selected from fluorine atom, chlorine atom, cyano, amino, hydroxyl, $C_{1-4}$ alkyl, halo $C_{1-4}$ alkyl, hydroxyl $C_{1-4}$ alkyl, or $C_{1-4}$ alkoxy.

8. The compound according to claim 7, pharmaceutically acceptable salts or stereoisomers thereof:
$R^1$ is selected from the following groups:

$R^3$ and $R^4$ are independently selected from hydrogen;
m is 0 or 1;
Z is sodium ion;

R⁵ is selected from the following groups:
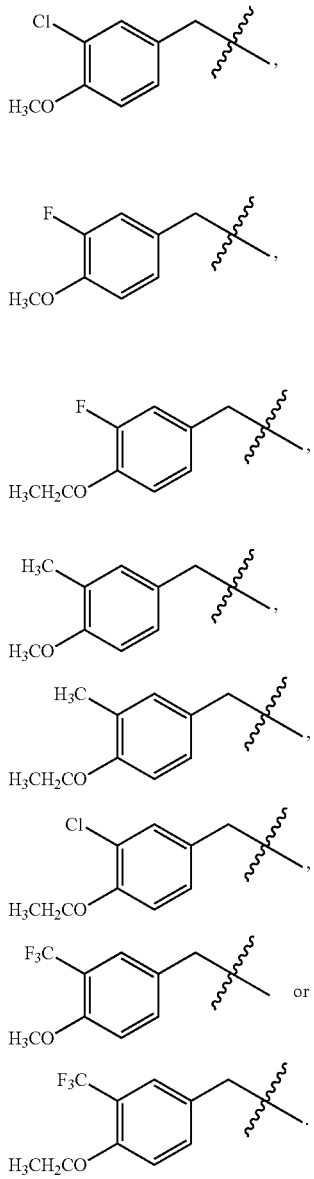
9. The compound according to claim 1, pharmaceutically acceptable salts or stereoisomers thereof, the compound being selected from:
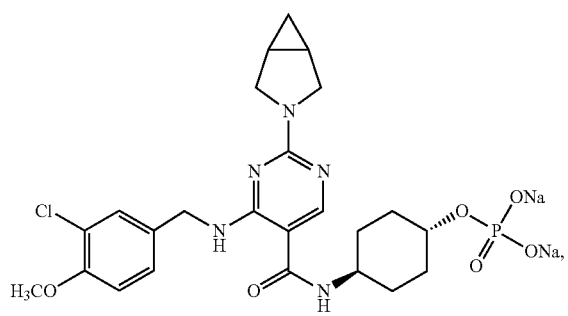
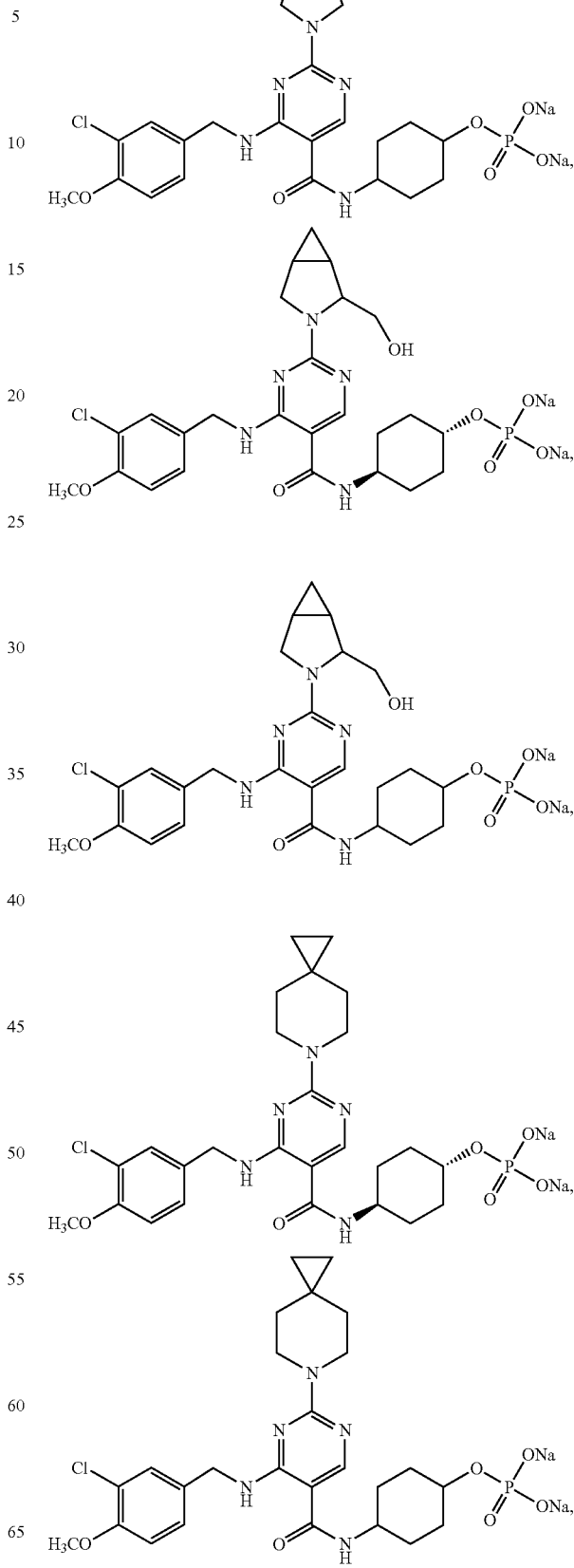

61
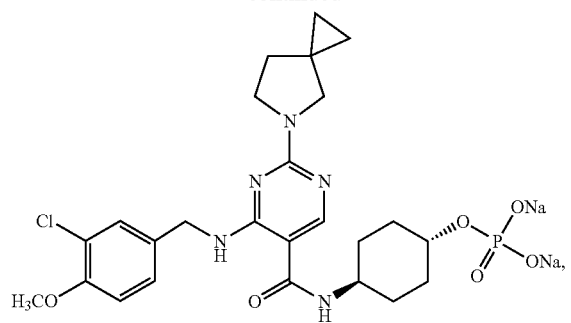
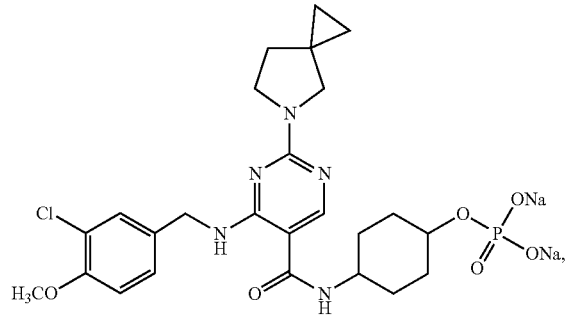
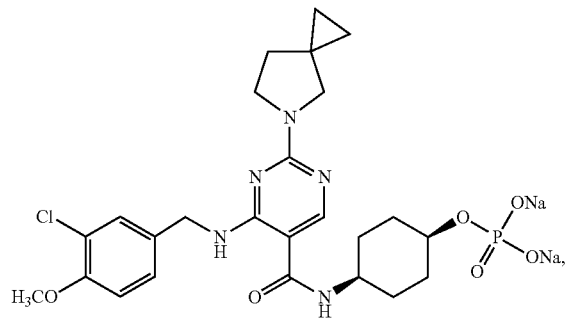
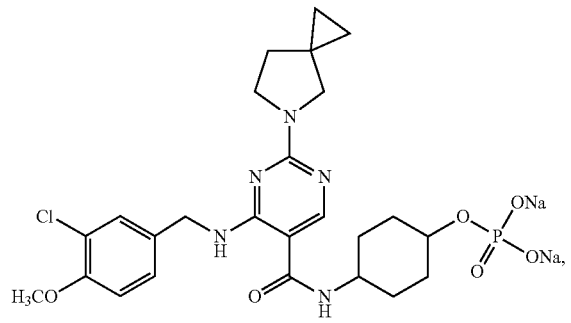
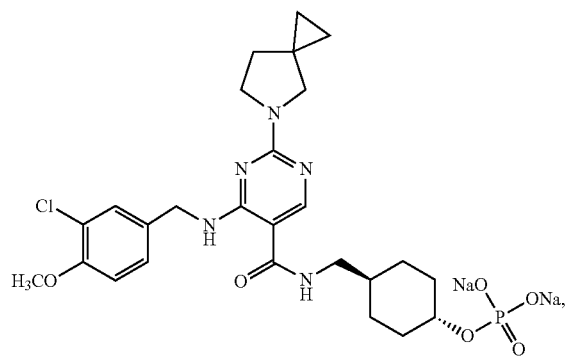
62
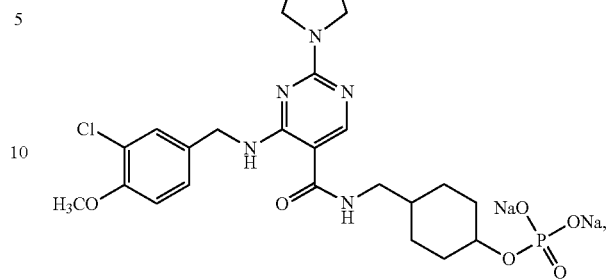
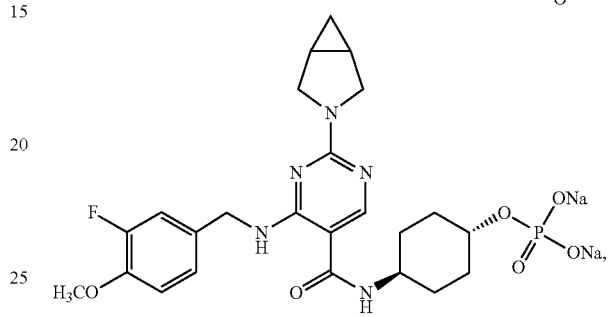
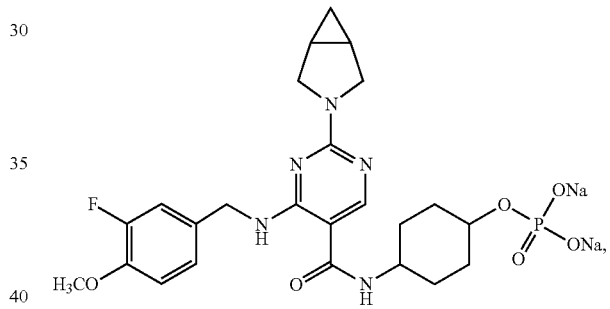
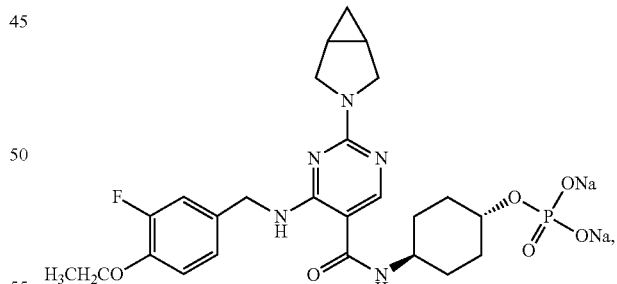
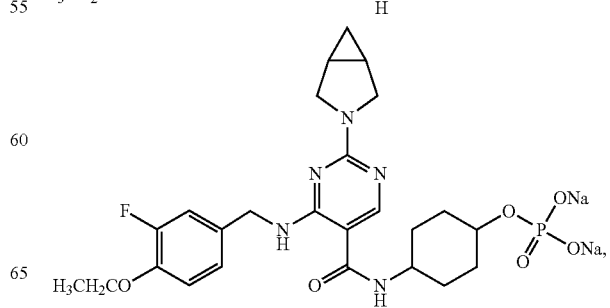

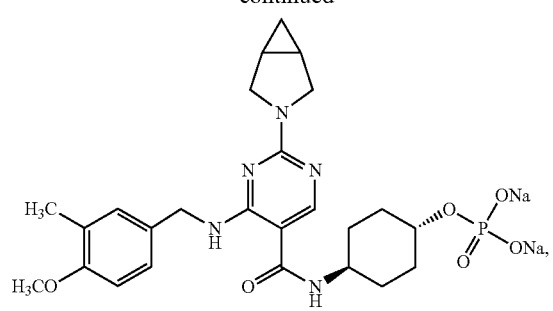
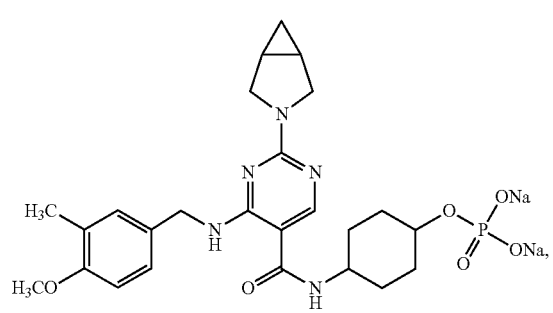
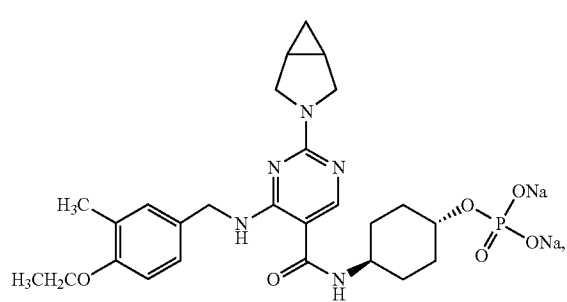
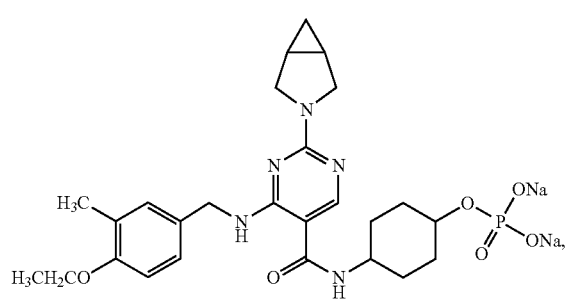
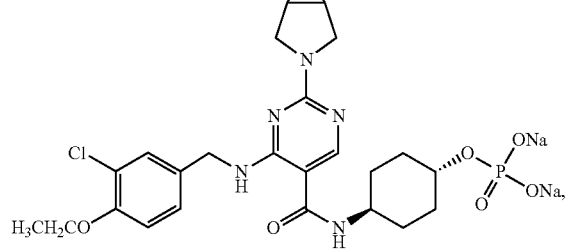

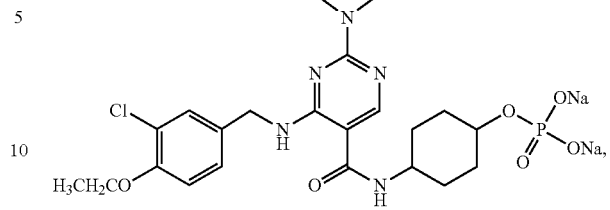
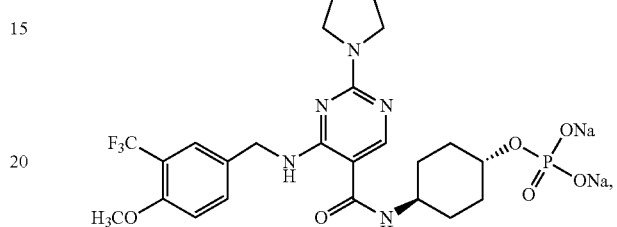
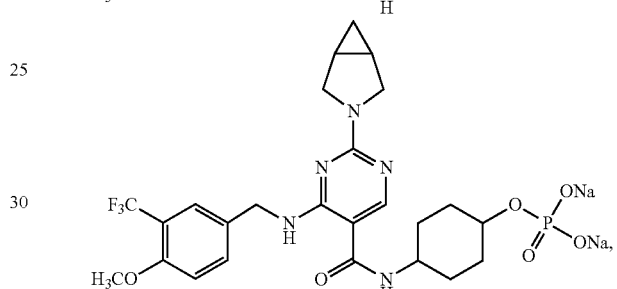
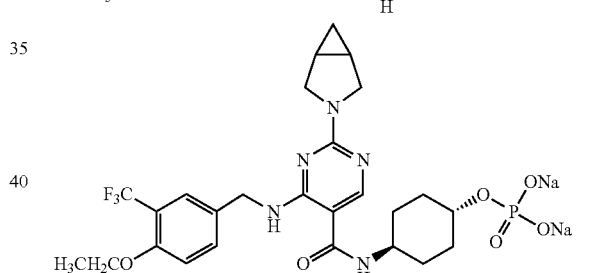

or

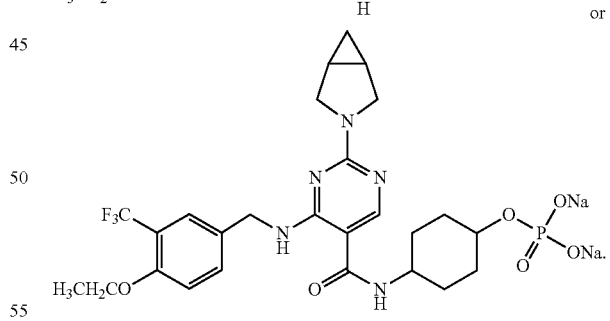

10. A pharmaceutical preparation comprising the compound of claim 1, pharmaceutically acceptable salts or stereoisomers thereof, and one or more pharmaceutically acceptable carriers and/or diluents.

11. A pharmaceutical composition comprising the compound of claim 1, pharmaceutically acceptable salts or stereoisomers thereof, characterized in further comprising one or more second therapeutically active agents selected from vasodilators, prostaglandin E1, prostacyclin, α-adrenergic receptor retardants, mixed α,β-blockers, α-blockers, 5α-reductase inhibitors, α2-adrenergic receptor retardants, ACE inhibitors, NEP inhibitors, central dopamine agents, vasoactive intestinal peptide, calcium channel blockers, thiazines, or mixtures thereof.

12. A method of treating erectile dysfunction and lower urinary tract symptoms, said method comprising the step of administering the compound of claim 1, pharmaceutically acceptable salts or stereoisomers thereof.

13. A method of treating diseases selected from: hypertension, heart failure, pulmonary hypertension, erectile dysfunction, overactive bladder syndrome, and prostatic hyperplasia, said method comprising the step of administering the compound of claim 1, pharmaceutically acceptable salts or stereoisomers thereof.

14. The method of claim 12, wherein the disease is overactive bladder syndrome and benign prostatic hyperplasia.

15. The method of claim 13, wherein the disease is overactive bladder syndrome and benign prostatic hyperplasia.

16. A method of manufacturing a medicament, said method comprising the step of mixing the compound of claim 1, pharmaceutically acceptable salts or stereoisomers thereof with a pharmaceutically acceptable carrier.

17. A method of synthesizing the compound of Formula (I), pharmaceutically acceptable salts or stereoisomers as set forth in claim 1, said method comprising the steps of:

I. reacting a first raw material with a second raw material in the presence of a first organic solvent and a first organic alkali to form a first intermediate according to the following reaction:

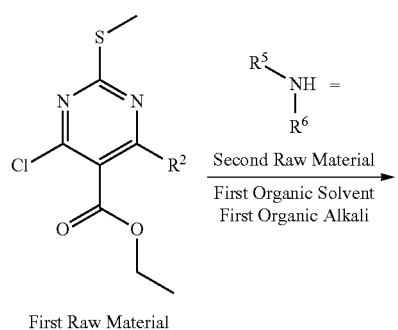

First Raw Material

II. reacting the first intermediate with m-chloroperoxybenzoic acid (mCPBA) in the presence of a second organic solvent to form a second intermediate according to the following reaction:

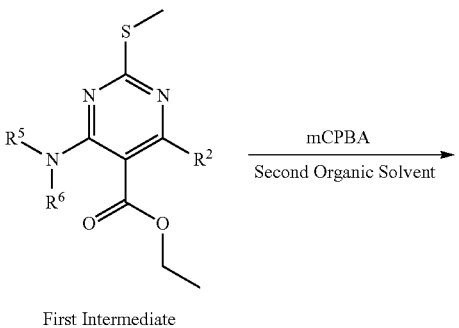

First Intermediate

III. reacting the second intermediate with a third raw material in the presence of a second organic alkali to form a third intermediate according to the following reaction:

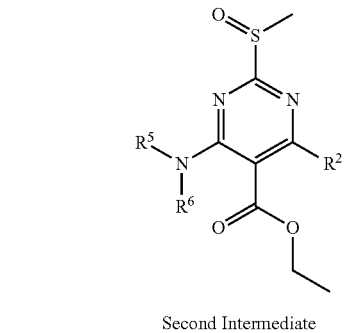

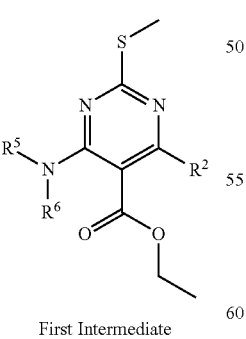

First Intermediate

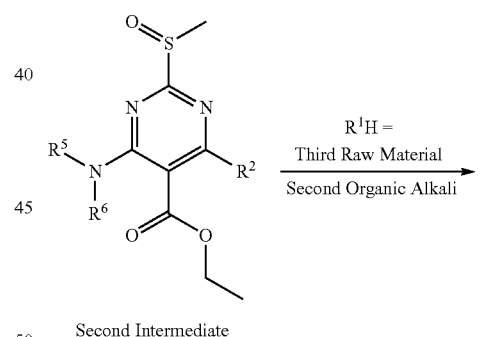

Second Intermediate

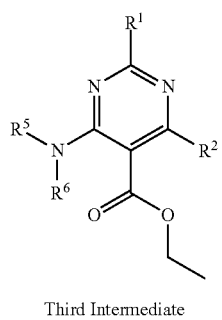

Third Intermediate

IV. hydrolyzing the third intermediate in the presence of a third organic solvent and an first inorganic alkali to form a fourth intermediate according to the following reaction:

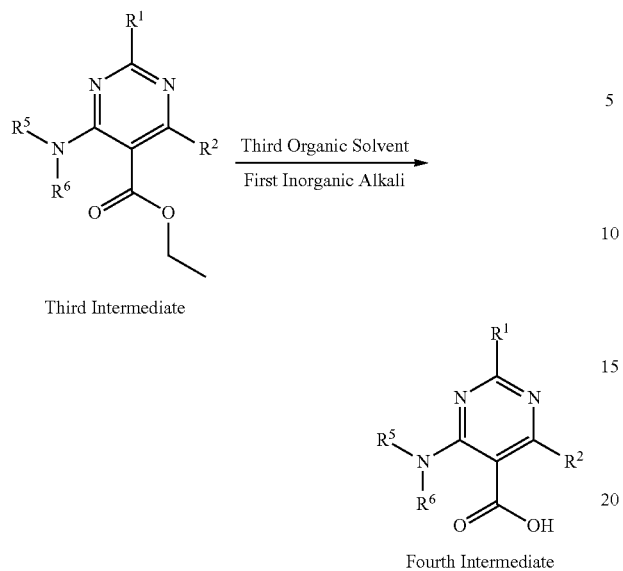

Third Intermediate

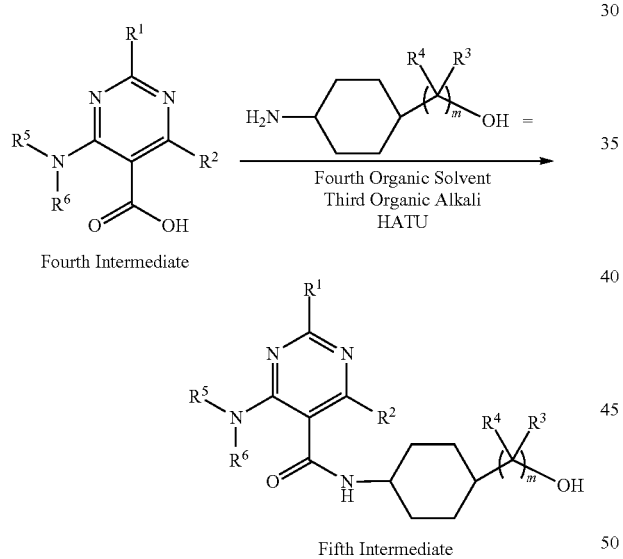

Fourth Intermediate

V. reacting the fourth intermediate with a fourth raw material in the presence of a fourth organic solvent, a third organic alkali, and HATU to form a fifth intermediate according to the following reaction:

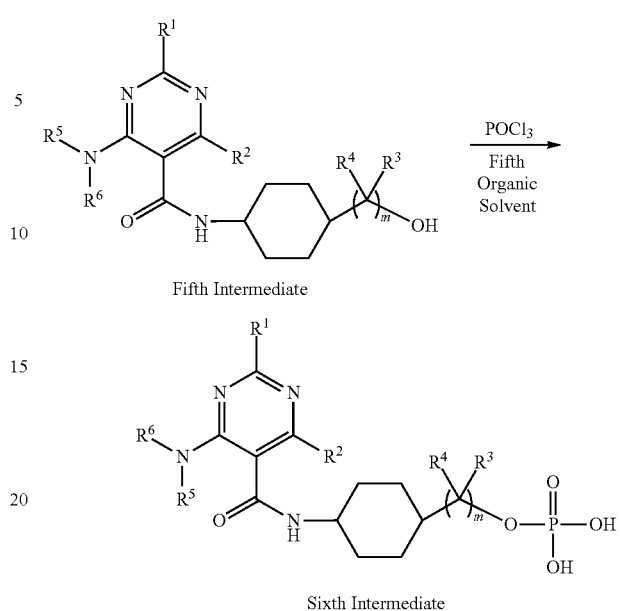

Fifth Intermediate

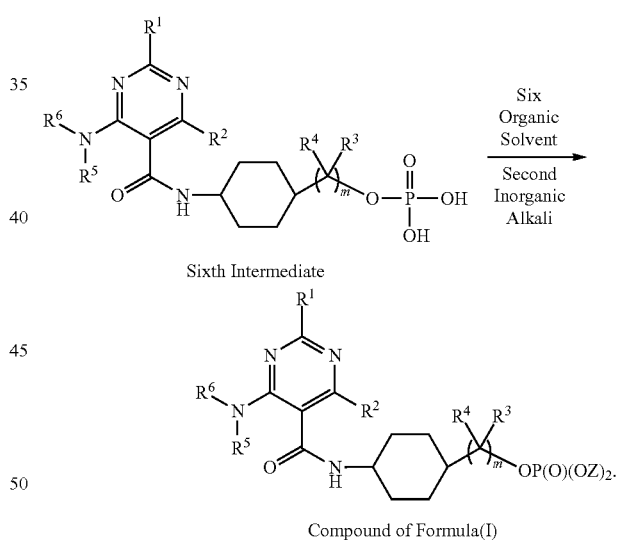

Sixth Intermediate

VI. reacting the fifth intermediate with phosphoryl chloride in the presence of a fifth organic solvent to form a sixth intermediate according to the following reaction:

VII. basifying the sixth intermediate in the presence of a sixth organic solvent and a second inorganic alkali to form the compound of claim 1 according to the following reaction:

* * * * *